United States Patent [19]

Brewster et al.

[11] Patent Number: 4,921,866
[45] Date of Patent: May 1, 1990

[54] 1,3-DIOXANES

[75] Inventors: Andrew G. Brewster, Macclesfield; George R. Brown, Wilmslow; Reginald Jessup, Sandbach; Michael J. Smithers, Macclesfield, all of United Kingdom

[73] Assignee: Imperial Chemical Industries plc, London, England

[21] Appl. No.: 185,873

[22] Filed: Apr. 25, 1988

[30] Foreign Application Priority Data

Apr. 24, 1987 [GB] United Kingdom ............... 8709794

[51] Int. Cl.$^5$ .................. C07D 401/04; C07D 40/06; A61K 31/44
[52] U.S. Cl. ..................................... 514/336; 546/268
[58] Field of Search ..................... 546/268; 514/336

Primary Examiner—Jane T. Fan
Attorney, Agent, or Firm—Cushman, Darby & Cushman

[57] ABSTRACT

The invention concerns novel, pharmaceutically useful 1,3-dioxane alkanoic and alkenoic acid derivatives of the formula I in which the groups at positions 2, 4 and 5 of the 1,3-dioxane ring have cis-relative stereochemistry, Y is ethylene or vinylene, n is 1-4, Z is hydrogen or hydroxy, and X is a pyridine containing group (as defined hereinafter); and the pharmaceutically acceptable salts thereof. The invention also includes processes for the manufacture and use of the acid derivatives as well as pharmaceutical compositions for therapeutic use in one or more of a variety of diseases such as ischaemic heart disease, cerebrovascular disease, asthmatic disease and/or inflammatory disease.

15 Claims, No Drawings

1,3-DIOXANES

This invention concerns novel 1,3-dioxanes and, more particularly, it concerns novel 1,3-dioxane-5-yl alkanoic acids containing a pyridine moiety attached at position 2 of the 1,3-dioxane ring. The acids of the invention have valuable pharmaceutical properties and the invention includes pharmaceutical compositions containing the novel acids and processes for the manufacture and medical use of the novel acids.

It is known that the arachidonic acid metabolite thromboxane $A_2$ (hereinafter referred to as "$TXA_2$") is a powerful vasoconstrictor and a potent aggregator of blood platelets. $TXA_2$ is also a potent constrictor of bronchial and tracheal smooth muscle. $TXA_2$ may therefore be involved in a variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance.

It is believed that $TXA_2$ exerts its physiological action through the thromboxane receptor at which receptor various other prostanoid contractile substances derived from arachidonic acid such as prostaglandins $H_2$, $F_2$ alpha and prostaglandin $D_2$ can exert contractile effects. There are two principal ways in which the effects of $TXA_2$ (and also of prostaglandins $H_2$, $F_2$ alpha and/or $D_2$) can be ameliorated. The first is by administering a pharmacological agent which preferentially occupies the thromboxane receptor, but yet does not produce the contractile effects which follow the binding of $TXA_2$ (or of prostaglandins $H_2$, $F_2$ alpha and/or $D_2$). Such an agent is said to possess $TXA_2$ antagonist properties. The second way is to administer a pharmacological agent which inhibits one or more of the enzymes involved in the production of $TXA_2$ and in particular which inhibits the enzyme known as thromboxane synthase ($TXA_2$ synthase). Such an agent is said to be a $TXA_2$ synthase inhibitor. Accordingly, it may be seen that agents which possess $TXA_2$ antagonist properties and/or which inhibit $TXA_2$ synthase may be expected to be of therapeutic value in the treatment of one or more of the above mentioned diseases or other diseases in which $TXA_2$ is involved. Also, agents which possess $TXA_2$ antagonist properties may be expected to be of value additionally in treating those diseases in which prostaglandins $H_2$, $F_2$ alpha and/or $D_2$ are involved, for example especially in asthmatic and inflammatory diseases. It is known from our European patent application Nos. 201352 and 201351 that 2-(styryl)1,3-dioxan-5-ylalkenoic acids and 2-(phenoxyalkyl)-1,3-dioxan-5-ylhexenoic acids, respectively, possess $TXA_2$ antagonist properties.

We have now discovered (and this is the basis for our invention) that certain 1,3-dioxan-5-yl alkenoic and alkanoic acids of the formula I (set out, together with the other chemical structures, at the end of this specification) containing a pyridine moiety attached at position 2 of the 1,3-dioxane ring surprisingly possess pharmacologically significant effects mediated at least in part via the $TXA_2$ receptor and resulting from antagonism at the $TXA_2$ receptor and/or inhibition of the enzyme $TXA_2$ synthase.

According to the invention there is provided a 1,3-dioxane alkanoic acid derivative of the formula I (set out hereinafter) wherein Y is ethylene or vinylene; n is the integer 1, 2, 3 or 4; Z is hydrogen or hydroxy; X is a pyridine containing group of the formula II (set out hereinafter) in which A is a linking group selected from (1–6C)alkylene and (2–6C)alkenylene, either of which may optionally be branched and may optionally contain an oxy link in place of one linking carbon atom, provided that the terminal atom in A attached to the 1,3-dioxane ring is always carbon, or A is a direct link to the 1,3-dioxane ring, and $R^1$, $R^2$ and $R^3$ are independently selected from hydrogen, halogeno, trifluoromethyl, (1–6C)alkoxy and (1–10C)alkyl optionally bearing a carboxy or (1–6C)alkoxy.carbonyl substituent; and wherein the groups at positions 2, 4 and 5 of the 1,3-dioxane ring have cis-relative stereochemistry; or a pharmaceutically acceptable salt thereof.

It will be appreciated that the compounds of formula I possess asymmetric carbon atoms and may exist and be isolated in racemic and optically active forms. The invention includes both the racemic forms and any optically active form (or mixtures thereof) which is capable of antagonising one or more of the actions of $TXA_2$ and/or inhibiting the synthesis of $TXA_2$, it being well known in the art how to prepare individual optical isomers (for example by synthesis from optically active starting materials or resolution of a racemic form) and how to determine the $TXA_2$ antagonist properties and $TXA_2$ synthase inhibitory properties using one or more of the standard tests referred to hereinafter.

Although a particular configuration is shown in the chemical formulae attached hereto this does not necessarily correspond to the absolute configuration.

A particular value for A when it is (1–6C)alkylene or (2–6C)alkenylene as defined above is, for example, methylene, ethylene, trimethylene, vinylene, propenylene, isopropylidene, 1,1-dimethylethylene, 2-methyl-1,2-propenylene, methyleneoxymethylene, oxymethylene, oxyethylene, oxyisopropylidene (—$O.C(CH_3)_2$—), trimethyleneoxyethylene (—$(CH_2)_3.O.(CH_2)_2$—) or a group of the formula —$CH_2.O.CH_2.C(CH_3)_2$.— or —$O.CH_2.C(CH_3)_2$.—.

It will be understood that when A contains a terminal oxy then that constituent is attached to the pyridine moiety rather than to the 2-position of the dioxane moiety.

Specific values of A of particular interest include, for example, when it is a direct bond, methylene, isopropylidene, ethylene, 1,1-dimethylethylene (especially wherein the unsubstituted methylene constituent is attached to the pyridine moiety), oxymethylene, oxyethylene or oxyisopropylidene.

Particular values for $R^1$, $R^2$, or $R^3$ include, for example: for halogeno: fluoro, chloro or bromo; for (1–6C)alkoxy: methoxy, ethoxy, propoxy or butoxy; and for (1–10C)alkyl: (1–4C)alkyl or (5–10C)alkyl, including, for example, methyl, ethyl, propyl, isopropyl, butyl, pentyl, hexyl, heptyl, octyl, nonyl and decyl.

A particular value for $R^1$, $R^2$, or $R^3$ when it is (1–10C)alkyl bearing a carboxy or alkoxycarbonyl substituent is, for example, pentyl, hexyl, octyl, nonyl or decyl bearing a carboxy or alkoxycarbonyl substituent and, particularly, bearing such a substituent located at the end of the alkyl chain, for example 8-carboxyoctyl or 10-carboxydecyl, or the corresponding methyl or ethyl esters thereof.

A particular group of novel compounds of the invention comprises pyridyl derivatives of the formula III wherein A, Z and $R^1$ have any of the meanings defined hereinbefore, m is the integer 2 or 3, and the groups at positions 2, 4 and 5 of the 1,3-dioxane ring have cis-relative stereochemistry, and the pharmaceutically acceptable salts thereof.

Further groups of novel compounds of the invention of particular interest include the following:

(a) compounds of the formula III defined above wherein in addition Z is hydroxy and the linking group A (which preferably has a disubstituted methylene adjacent to the dioxane ring) is attached to the 3 or 4 position of the pyridine moiety;

(b) compounds of the formula III defined above wherein in addition Z is hydroxy, the linking group A is ethylene or vinylene and is attached to the 3 or 4 position of the pyridine moiety;

(c) compounds of formula III as defined above wherein in addition Z is hydroxy, the linking group A (which preferably has a disubstituted methylene adjacent to the dioxane ring) is attached to the 2 position of the pyridine moiety and m is the integer 2; and (d) compounds of the formula I defined above wherein in addition Z is hydrogen, n is the integer 2 or 3, and the linking group A (which is preferably a direct bond or methylene) is attached to the 3 or 4 position of the pyridine moiety;

together in each group with the pharmaceutically acceptable salts thereof.

The compounds of groups (a) and (b) above are of interest as being both $TXA_2$ antagonists and inhibitors of $TXA_2$ synthase. The compounds of group (c) above are of interest as $TXA_2$ antagonists without any significant $TXA_2$ synthase inhibitory properties. The compounds of group (d) above are of interest as being predominantly inhibitors of $TXA_2$ synthase.

In general, in the formula I compounds, when good $TXA_2$ antagonist properties are required, for example, a preferred value for Y is cis-vinylene, for n is the integer 2 or 3, (of which the integer 2 is particularly preferred) for Z is hydroxy and for A is a direct bond, methylene, ethylene, isopropylidene, 1,1-dimethylethylene and oxyisopropylidene; and when such properties are required coupled with synthase inhibition, additionally X contains a 3- or 4-pyridyl moiety. Similarly, when predominantly $TXA_2$ synthase inhibitory properties are required, for example, a preferred value for n is the integer 2 or 3, for Z is hydrogen and for A is a direct bond or methylene.

It is generally preferred that the total carbon content of $R^1$, $R^2$ and $R^3$ taken together is not more than 12 carbon atoms. It is also generally preferred that only one of $R^1$, $R^2$ and $R^3$ is alkyl.

Specific values for $R^1$, $R^2$ and $R^3$ include, for example, hydrogen, methyl, ethyl, propyl, butyl, pentyl, heptyl, methoxy, ethoxy, trifluoromethyl, fluoro, chloro and bromo. A preferred value for $R^1$, $R^2$ or $R^3$ is, for example, hydrogen or methyl of which hydrogen is especially preferred.

Particular values for the pyridyl moiety in formula II include, for example, 2-pyridyl, 3-pyridyl or 4-pyridyl optionally bearing one or two substituents selected from (1–4C)alkyl, (1–4C)alkoxy, halogeno and trifluoromethyl. A particularly preferred pyridyl moiety is 3- or 4-pyridyl optionally bearing a (1–4C)alkyl substituent such as methyl. A particularly preferred pyridyl moiety for compounds of the invention which are $TXA_2$ antagonists without any significant $TXA_2$ synthase inhibitory properties, is 2-pyridyl.

Particular novel compounds of the invention are described in the accompanying Examples. Of these, the compounds of Examples 4 and 11 are of particular interest by virtue of their $TXA_2$ antagonist properties, the compounds of Examples 1, 2, 12, 17, 18, 19 and 23 by virtue of their combined antagonist and $TXA_2$ synthase inhibitory properties, and the compounds of Examples 9 and 16 by virtue of their predominantly $TXA_2$ synthase inhibitory properties. These compounds are provided, together with their pharmaceutically acceptable salts thereof as a further feature of the invention.

It will be appreciated that the compounds of formula I are amphoteric and can form salts with acids as well as bases. Particular pharmaceutically acceptable salts therefore include, for example, alkali metal and alkaline earth metal salts, ammonium and aluminium salts, salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide, and also salts with acids affording physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be manufactured by conventional procedures of organic chemistry well known in the art for the manufacture of structurally analogous compounds. Such procedures are provided as a further feature of the invention and are illustrated by the following representative procedures in which X, Y, Z, n, A and $R^1$-$R^3$ have any of the meanings defined hereinbefore.

(a) For a compound of the formula I wherein Z is hydroxy, a phenol derivative of the formula IV wherein P is a protecting group, for example (1–6C)alkyl (such as methyl or ethyl), acyl (such as acetyl, benzoyl, methanesulphonyl or p-toluenesulphonyl), allyl, tetrahydropyran-2-yl, trialkylsilyl (such as trimethylsilyl or t-butyldimethylsilyl), is deprotected. A preferred protecting group is, for example, acyl and in particular methanesulphonyl or p-toluenesulphonyl.

The deprotection conditions used depend on the nature of the protecting group P. Thus, for example, when P is methyl or ethyl the deprotection may be carried out by heating with sodium thioethoxide in a suitable solvent (such as N,N-dimethylformamide or N,N-dimethyl-3,4,5,6-tetrahydro-2(1H)-pyrimidinone) at a temperature in the range, for example, 50° to 160° C. Alternatively, an ethyl or methyl protecting group may be removed by reaction with lithium diphenylphosphide in a suitable solvent (such as tetrahydrofuran or methyl t-butyl ether) at a temperature in the range, for example, 0° to 60° C. When the protecting group P is acyl, it may be removed, for example, by hydrolysis in the presence of a base (such as sodium or potassium hydroxide) in a suitable aqueous solvent [such as an aqueous (1–4C)alkanol (e.g. methanol) or ether (e.g. tetrahydrofuran)] at a temperature in the range, for example, 0° to 60° C. When the protecting group P is allyl or tetrahydropyran-2-yl, it may be removed, for example, by treatment with strong acid such as trifluoroacetic acid and when it is trialkylsilyl, it may be removed, for example, by reaction with aqueous tetrabutylammonium fluoride or sodium fluoride optionally together with an ether such as tetrahydrofuran or t-butyl methyl ether, using a conventional procedure.

(b) For a compound of the formula I wherein Y is vinylene, an aldehyde of the formula V is reacted with a Wittig reagent of the formula: $R_3P=CH.(CH_2)_n.CO_2^-M^+$ wherein R is (1–6C)alkyl or aryl (especially phenyl) and $M^+$ is a cation, for example an alkali metal cation such as the lithium, sodium or potassium cation.

The process in general produces the required compounds of formula I in which the substituents adjacent to the double bond have predominantly the preferred cis-relative stereochemistry i.e. as the "Z" isomer. However the process also produces generally small amounts of the analogous compounds having trans-relative stereochemistry (i.e. the "E" isomer) which may be removed by a conventional procedure such as chromatography or crystallisation.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, $-80°$ C. to $40°$ C., but is conveniently performed at or near room temperature, for example in the range $0°$ to $35°$ C.

(c) An erythro-diol derivative of the formula VI wherein one of $Q^1$ and $Q^2$ is hydrogen and the other is hydrogen or a group of the formula -CRaRb.OH [wherein Ra and Rb are the same or different (1–4C)alkyl] is reacted with an aldehyde derivative of the formula VII, or an acetal, hemiacetal or hydrate thereof.

The aldehyde VII [or its hydrate, or its acetal or hemiacetal with a (1–4C)alkanol (such as methanol or ethanol)] may conveniently be present in an excess.

The reaction is generally performed in the presence of an acid catalyst (at least one molecular equivalent of which is normally required because of the basicity of the pyridine moiety) such as hydrogen chloride, hydrogen bromide, sulphuric acid, phosphoric acid, methanesulphonic acid or p-toluenesulphonic acid, conveniently in the presence of a suitable solvent or diluent, such as acetonitrile, dichloromethane, toluene, xylene or an ether, for example tetrahydrofuran, dibutyl ether, methyl t-butyl ether or 1,2-dimethoxyethane, and at a temperature in the range, for example, $0°$ to $80°$ C.

Those starting materials of formula VI wherein $Q^1$ and $Q^2$ are both hydrogen may be obtained, for example, by mild, acid catalysed, hydrolysis or alcoholysis of the dioxane ring of a compound of formula VIII wherein Ra and Rb are both alkyl such as methyl or ethyl, obtained by an analogous procedure to process (b) herein, for example as described in European patent application, Publication No. 94239. The hydrolysis or alcoholysis will normally be carried out at a temperature in range $10°$ to $80°$ C. using an aqueous mineral acid such as hydrochloric acid in an alkanol such as ethanol or 2-propanol or an ether (such as tetrahydrofuran) as solvent.

The starting materials of formula VI wherein one of $Q^1$ and $Q^2$ is hydrogen and the other is a group of the formula—$CRaRb.OH$ are intermediates in the above-mentioned formation of the starting materials of formula VI wherein $Q^1$ and $Q^2$ are both hydrogen. However, said intermediates are not normally isolated or characterised. Accordingly, the invention also provides a modified procedure (d) of process (c) which comprises reacting a compound of formula VIII wherein one of Ra and Rb is hydrogen, methyl or ethyl and the other is methyl or ethyl with an excess of the aldehyde of formula VII (or a hydrate, acetal or hemiacetal thereof) in the presence of an acid catalyst (such as one of those given above), conveniently at a temperature in the range, for example, $10°$ to $80°$ C. and, optionally, in the presence of a suitable solvent or diluent (such as one of those given above).

(e) For a compound of the formula I wherein Y is ethylene, a compound of the formula I wherein Y is vinylene is hydrogenated in the presence of a suitable catalyst.

The process is normally carried out in a suitable solvent or diluent, for example, a (1–4C)alkanol such as ethanol or 2-propanol, optionally in the presence of water and at a temperature in the range, for example, $15°$ to $35°$ C., using hydrogen at a pressure of, for example, about 1–2 bar. A particularly suitable catalyst is, for example, a noble metal catalyst such as palladium or platinum conveniently on an inert support such as carbon, barium sulphate or barium carbonate. The process is not generally suitable for the production of those compounds of formula I wherein A is a readily reducible alkenyl.

The starting materials for use in the above processes may be made by general procedures of organic chemistry, known for the production of structurally related compounds, for example as illustrated in the accompanying Examples. For example, the aldehydes of formula V may be obtained, for example, by the method shown in Scheme I. The protected phenol derivatives of formula IV may be made, for example, by using an analogous procedure to process (b) above using an aldehyde analogous to that of formula V, but wherein the phenol group has been protected with the group P, such an aldehyde being made, for example, by carrying out the procedures of Scheme I omitting the deprotection step. Alternatively, the compounds of formula IV may be obtained by an analogous procedure to process (d) above using a protected version of the dioxane of formula VIII. Those of the starting materials of formula VIII which are novel may be obtained using analogous procedures to those described in European patent application, Publication No. 94239. The aldehydes of formula VII may be made by standard procedures of organic chemistry well known in the art.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (b) above.

It will be understood that the compounds of formula I may also be obtained by other conventional procedures well known in the art, for example by base catalysed hydrolysis of the corresponding esters, amides or nitriles. Such procedures are also within the ambit of the invention.

Whereafter, when a salt of a compound of formula I is required, it may be obtained by reaction with the appropriate base or acid affording a physiologically acceptable ion, or by any other conventional salt formation procedure.

Further, when an optically active form of a compound of formula I is required, one of the aforesaid processes may be carried out using an optically active starting material. Alternatively, the racemic form of a compound of formula I may be resolved by reaction with an optically active form of a suitable organic base or acid, for example ephedrine, N,N,N-trimethyl(1-phenylethyl)ammonium hydroxide, 1-phenylethylamine, tartaric or camphorsulphonic acid, followed by conventional separation of the diastereoisomeric mixture of salts thus obtained, for example by fractional crystallisation from a suitable solvent, for example a (1–4C)alkanol, whereafter the optically active form of said compound of formula I may be liberated by the appropriate treatment with acid or base using a conventional procedure, for example using an aqueous mineral acid such as dilute hydrochloric acid (or aqueous alkali such as aqueous sodium hydroxide).

Many of the intermediates defined herein are novel, for example those of formulae IV and V, and are provided as further, separate features of the invention. In addition, certain of the compounds of the formula IV, such as those described within the Examples hereinafter, possess useful pharmacological properties in their own right, for example $TXA_2$ synthase inhibitory properties at concentrations of $10^{-6}M$ or less.

As stated earlier, the compounds of formula I possess significant $TXA_2$ antagonist properties and/or are inhibitors of $TXA_2$ synthase. The $TXA_2$ antagonism may be demonstrated in one or other of the following standard tests:

(a) The rat aortic strip model (based on that devised by Piper and Vane (Nature, 1969, 223, 29–35) in the rabbit) using as agonist the $TXA_2$ mimetic agent known as U46619 (described by R. L. Jones et alia in "Chemistry, Biochemistry and Pharmacological Activity of Prostanoids" edited by S. M. Roberts and F. Scheinmann, at page 211; Pergamon Press, 1979);

(b) a blood platelet aggregation test based on that described by Born (Nature, 1962, 194, 927–929) and involving:

(i) aggregating human, citrated, platelet-rich plasma by addition of the $TXA_2$ mimetic agent U46619 so that a dose-response curve is generated;

(ii) generating a dose-response curve for U46619 stimulated platelet aggregation in the presence of increasing amounts of test compound (generally in the range $10^{-5}M$ to $10^{-10}M$); and (iii) calculating a $K_B$ value indicating potency of $TXA_2$ antagonism for the test compound, average over several concentrations, from the calculated 50% response value for U46619 aggregation in the presence and absence of test compound; or (c) a bronchoconstriction test involving measuring the inhibition by a test compound of the bronchoconstriction induced in the Konzett-Rossler, anaesthetised guinea-pig model (as modified by Coller and James, Brit. J. Pharmacol., 1967, 30, 283–307) by intravenous administration of the $TXA_2$ mimetic agent, U46619 and involving:

(i) obtaining a cumulative dose-response curve to U46619 induced bronchoconstriction by intravenous administration of constant volumes of increasing concentrations of U46619 (0.2–4 μg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

Test (b) may conveniently be modified to demonstrate the antagonism of the effects of $TXA_2$ in vivo by assessing the effects of a test compound on the aggregation of blood platelets obtained after administration of test compound to a laboratory animal, such as a rabbit, rat, guinea pig or dog. However, when the aggregation of dog platelets is being studied it is necessary to add a predetermined, threshold concentration of the platelet aggregation agent adenosine diphosphate (about $0.4–1.2 \times 10^{-6}M$) before addition of the $TXA_2$ mimetic agent, U46619.

The antagonism of the effects of $TXA_2$ on the vasculature may also be demonstrated, for example in rats in the following procedure (d):

Male rats (Alderley Park strain) are anaesthetised with sodium pentobarbital and blood pressure is monitored at the carotid artery. The $TXA_2$ mimetic agent U46619 is administered intravenously at 5 μg/kg via the jugular vein to produce 20–30 mm/Hg (2640–3970 pascal) increase in systolic blood pressure. The process is repeated twice to ensure adequacy of response. A test compound is then administered either intravenously (via the jugular vein) or orally (via a cannula) directly into the stomach and the animal challenged with U46619, five minutes after dosing with test compound and then successively every ten minutes until the hypertensive effect of U46619 is no longer blocked.

The $TXA_2$ synthase inhibitory properties of a test compound may be demonstrated using the standard in vitro test procedure [test (e)] described by Howarth et alia (Biochem. Soc. Transactions, 1982, 10, 239–240) using a human platelet microsomal $TXA_2$ synthase preparation and using a quantitative thin layer radiochromatographic method to assess the conversion of [1-$^{14}$C]arachidonic acid to the $TXA_2$ metabolite thromboxane $B_2$ ($TXB_2$).

The $TXA_2$ synthase inhibitory and $TXA_2$ antagonist properties of a test compound may also be demonstrated in a standard procedure (f) involving obtaining blood samples from laboratory animals (typically rats, but also guinea pigs, rabbits or dogs) dosed with the test compound, generally by the oral route. The samples treated with anti-coagulant are first incubated at 37° C. with collegen (at about 100 micro M), then mixed with the cyclooxygenase inhibitor indomethancin (at about $10^3M$), centrifuged and the level of the $TXA_2$ metabolite $TXB_2$ determined by a standard radioimmunoassay technique. By comparison of the amount of $TXB_2$ present in the plasma from animals dosed with test compound with that in the plasma of a control group dosed with placebo, the $TXA_2$ synthase inhibitory properties may be assessed. Equally, the $TXA_2$ antagonist properties may be determined from the same blood sample using the procedure of (b) above to determine a $K_B$ value.

Many of the compounds of formula I, for example those compounds wherein the X group is a group of the formula 3-(or 4)-pyridyl.A-, surprisingly possess both $TXA_2$ antagonist properties and $TXA_2$ synthase inhibitory properties.

In general, compounds of formula I show effects in the following ranges in one or more of the above tests:

test (a): $pA_2$ of $>5.8$ (b): $K_B$ of $>1.0\times 10^{-6}M$ test (c): dose ratio of $>5$, 1 hour after dosing at 10 mg/kg test (d): significant inhibition of U46619 induced hypertension for at least 1 hour following oral dosing at 50 mg/kg or less test (e): $IC_{50}$ of $>1\times 10^{-5}M$ test (f): significant inhibition of $TXB_2$ production and a $K_B$ of $>1.0\times 10^{-6}M$, 1 hour following a dose of 100 mg/kg or less.

No overt toxic or other untoward effects have been observed with representative compounds of formula I having effects in in vivo tests (c), (d) or (f) at several multiples of the minimum effective dose.

By way of illustration, the compound of Example 1 hereinafter possesses both $TXA_2$ antagonist and $TXA_2$ synthase inhibitory properties as indicated by a $pA_2$ of 7.1 in test (a), a $K_B$ of $1.7\times 10^{-8}M$ in test (b), an $IC_{50}$ of $3.14\times 10^{-6}M$ in test (e) and shows essentially complete inhibition of $TXB_2$ production 3 hours following an oral dose of 100 mg/kg to rats in test (f) without any observable signs of toxicity to the test animals.

As stated previously, by virtue of their effects on the $TXA_2$ system (i.e. $TXA_2$ antagonist and/or $TXA_2$ synthase inhibitory properties), the compounds of formula I may be used in the therapy or prevention of diseases or adverse conditions in warm-blooded animals in which $TXA_2$ (or prostaglandins $H_2$, $D_2$ and/or $F_2$ alpha) are involved. In general, a compound of formula I will be administered for this purpose by an oral, rectal, intravenous, subcutaneous, intramuscular or inhalation route, so that a dose in the range, for example 0.01–5 mg/kg body weight, will be given up to four times per day, varying with the route of administration, the severity of the condition and the size and age of the patient under treatment.

The compounds of formula I will generally be used in the form of a pharmaceutical composition comprising a compound of formula I or, a pharmaceutically acceptable salt thereof as defined hereinabove, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimize contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, beta-adrenergic blocker, thrombolytic agent or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition. Still further, a known $TXA_2$ antagonist, such as a preferred compound described in European patent application, Publication No. 201354, or a known $TXA_2$ synthase inhibitor such as dazoxiben or furegrelate [U63557] may be present in addition to a compound of the formula I, or a pharmaceutically acceptable salt thereof, in a composition according to the invention in order to modify the overall balance of $TXA_2$ antagonist and/or $TXA_2$ synthase inhibitory effects for the required therapeutic effect in any of the aforesaid diseases or disease conditions.

In addition to their use in therapeutic medicine, the compounds of formula I are also useful as pharmacological tools in the development and standardisation of test systems for the evaluation of the effect of $TXA_2$ in laboratory animals such as cats, dogs, rabbits, monkeys, rats and mice, as part of the search for new therapeutic agents. The compounds of formula I may also be used because of their $TXA_2$ antagonist and/or synthase inhibitory properties in helping to maintain the viability of blood and blood vessels in warm-blooded animals (or parts thereof) under-going artificial extracorporeal circulation, for example during limb or organ transplants. When used for this purpose a compound of formula I, or a physiologically acceptable salt thereof, will generally be administered so that a steady state concentration in the range, for example, 0.1 to 10 mg. per litre is achieved in the blood.

The invention will now be illustrated by the following non-limiting Examples in which, unless otherwise stated.

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on Fluka Kieselgel 60 (catalogue no. 60738) obtained from Fluka AG, Buchs, Switzerland CH-9470;

(iv) yields are given for illustration only and are not necessarily the maximum attainable by diligent process development;

(v) proton NMR spectra were normally determined at 200 MHz in a deuterated solvent using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet; and (vi) all end-products were isolated as racemates and characterised by microanalysis, NMR and/or mass spectroscopy.

EXAMPLE 1

Ethane thiol (0.733 ml) was added dropwise over 15 minutes to a stirred suspension of sodium hydride (473 mg, 50% w/w dispersion in mineral oil) in 1,3-dimethyl-3,4,5,6-tetrahydro-2(1H)-pyrimidone (DMPU) (15 ml)

at 4° C., under argon. The mixture was heated to 100° C. when a solution of 4(Z)-6-([2,4,5-cis]-4-o-methoxyphenyl-2-[3-pyridyl]-1,3-dioxan-5-yl)-hexenoic acid (630 mg) in DMPU (5 ml) was added and then maintained at 100° C. for 5 hours. The reaction mixture was cooled to ambient temperature and poured and ice-water (50 ml) and washed with dichloromethane (2×20 ml). The aqueous phase was acidified to pH 4 with 2M hydrochloric acid and extracted with ether (3×25 ml). These extracts were washed successively with water (2×20 ml) and saturated brine (20 ml), then dried (MgSO4) and evaporated. Flash chromatography of the residue, eluting with 1% v/v acetic acid in ethyl acetate, and a further purification by MPLC, eluting with dichloromethane/methanol-acetic acid (97:2.5:0.5 v/v), gave an amorphous solid. Recrystallisation from ethyl acetate - hexane gave 4(Z)-6-([2,4,5-cis]-4-o-hydroxyphenyl-2-[3-pyridyl]-1,3-dioxan-5-yl)hexenoic acid (359 mg), mp 130°–131° C.; NMR (CDCl3): 1.91 (2H, m), 2.35 (4H, m), 2.70 (1H, m), 4.14 (1H, dm J=11 Hz), 4.30 (1H, dd J=11 1 Hz), 5.40 (2H, m), 5.50 (1H, d J=2 Hz), 5.81 (1H, s), 6.82 (1H, dd J=7,1 Hz) 6.90 (1H, td J=7,1 Hz), 7.00 (2H,b), 7.20 (2H, m), 7.40 (1H, m), 7.96 (1H, dt J=7, 1 Hz), 8.62 (1H, m), 8.83 (1H, bs); m/e: 370 (M+H)+.

The starting acid was obtained as follows:

(i) A solution of 4(Z)-6-(4-o-methoxyphenyl-2,2-dimethyl-1,3-dioxan-cis-5-yl)hexenoic acid§ (3.34 g) and 3-pyridinecarboxaldehyde (1.88 ml) in dichloromethane (100 ml) was treated with p-toluenesulphonic acid monohydrate (3.99 g) and the mixture stirred for 72 hours. Ether (250 ml) was added and the mixture extracted with 1M sodium hydroxide (3×25 ml). The combined aqueous extracts were acidified to pH5 with 2M hydrochloric acid and extracted with ether (3×25 ml). These extracts were washed with water (25 ml) and saturated brine (25 ml), then dried (MgSO4) and evaporated. The residue was purified by flash chromatography eluting with dichloromethane/methanol/acetic acid (95:5:1 v/v) to give a pale yellow oil (2.44 g). A solution of this oil in methanol (50 ml) was treated with p-toluenesulphonic acid monohydrate (1.33 g) and the mixture stirred for 16 hours when ether (150 ml) was added. The mixture was successively washed with 5% w/v sodium bicarbonate (3×50 ml), water (2×50 ml), saturated brine (50 ml), dried (MgSO4) and evaporated. The residue was purified by MPLC, eluting with 50% v/v ethyl acetate/hexane to give methyl 4(Z)-6-([2,4,5-cis]-4-o-methoxyphenyl-2-[3-pyridyl]-1,3-dioxan-5-yl)hexenoate as a clear oil (1.40 g); NMR (CDCl3): 1.67 (1H, m), 1.98 (1H, m), 2.28 (4H, m) 2.57 (1H, m), 3.63 (3H, s), 3.85 (3H, s), 4.15 (1H, dm J=11 Hz), 4.23 (1H, dd J=11,1 Hz), 5.30 (2H, m), 5.44 (1H, d J=2 Hz), 5.80 (1H, s), 6.87 (1H dd J=7,1 Hz), 6.97 (1H,td J=7,1 Hz), 7.26 (1H, td J=7,1 Hz) 7.33 (1H, m), 7.46 (1H, dd J=7, 1.5 Hz), 7.92 (1H, dt J=7,1.5 Hz, 8.62 (1H, dd J=4,1.5 Hz), 8.80 (1H, d J=1.5 Hz); m/e: 398 (M+H)+. [§ This acid is disclosed in Example 1 of European patent application, Publication No. 201354]

(ii) 1M Sodium hydroxide solution (18.9 ml) was added to a stirred solution of methyl 4(Z)-6-([2,4,5-cis]-4-o-methoxyphenyl-2-[3-pyridyl]-1,3-dioxan-5-yl) hexenoate (1.25 g) in methanol (20 ml). After 2 hours, water (75 ml) was added. The mixture was washed with ether (25 ml), then acidified to pH4 with 2N citric acid and extracted with further ether (3×25 ml). These extracts were washed with saturated brine (2×25 ml), dried (MgSO4) and evaporated. The residue was purified by MPLC, eluting with ethyl acetate/hexane/acetic acid (75:25:1 v/v) to give 4(Z)-6-([2,4,5-cis]-4-o-methoxyphenyl-2-[3-pyridyl]-1,3-dioxan-5-yl)hexenoic acid as a pale yellow oil (1.03 g) which slowly crystallized on standing, mp 142°–145° C.; NMR (CDCl3): 1.66 (1H, m), 1.98 (1H, m), 2.32 (4H, m), 2.60 (1H, m), 3.83 (3H, s), 4.13 (1H, dm J=11 Hz), 4.24 (1H, dd J=11,1.5 Hz), 5.23 (1H, m), 5.42 (1H, m), 5.46 (1H, d J=2 Hz), 5.81 (1H, s), 6.87 (1H, bd J=7 Hz), 6.97 (1H, td J=7,1 Hz), 7.07 (1H, b), 7.25 (1H, td J=7,1 Hz), 7.37 (1H, m), 7.45 (1H, dd J=7,1 Hz), 7.96 (1H, bd J=7 Hz), 8.60 (1 H,b), 8.82 (1H, b); m/e: 384 (M+H)+.

EXAMPLE 2

In a similar manner to Example 1, but starting with ethane thiol (0.89 ml), sodium hydride (0.58 g; 50% w/w oil dispersion), DMPU (25 ml) and 5(Z)-7-([2,4,5-cis]-4-o-methoxyphenyl-2-[3-pyridylmethyl]-1,3-dioxan-5-yl)heptenoic acid (0.822 g), there was obtained after flash chromatography using 1% v/v acetic acid in ethyl acetate as eluant, 5(Z)-7-([2,4,5-cis]-4-o-hydroxyphenyl-2-[3-pyridylmethyl]-1,3-dioxan-5-yl)heptenoic acid as a white solid (594 mg after recrystallisation from ethyl acetate), mp 179°–180° C.; NMR (CDCl3/D6-DMSO): 1.58 (3H, m), 1.84 (3H, m), 2.22 (3H, m), 3.07 (2H, d J=3.5 Hz), 3.90 (1H, dm J=11 Hz), 4.03 (1H, dd J=11,1 Hz), 5.01 (1H, t J=3.5 Hz), 5.14 (1H, m), 5.20 (1H, d J=2 Hz), 5.32 (1H, m), 6.82 (2H,m), 7.11 (2H, m), 7.32 (1H, m), 7.74 (1H, dm J=7 Hz), 8.50 (1H, bd J=4 Hz), 8.62 (1H, bs); m/e: 397 (M+).

The starting material was obtained as follows:

(i) Potassium t-butoxide (6.72 g) was added under argon to a stirred, ice-cooled mixture of 3-pyridylcarboxaldehyde (4.28 g) and (methyoxymethyl)triphenylphosphonium chloride (20.52 g) in dry tetrahydrofuran (THF). The mixture was stirred for 1 hour and was then poured into ice-water (100 ml). The mixture was extracted with ether (3×50 ml) and the extracts washed with water (2×50 ml), and saturated brine (50 ml), then dried (MgSO4) and evaporated. Flash chromatography, eluting with ether, gave a yellow oil (2.1 g). A solution of this oil (1.35 g) and methyl 5(Z)-erythro-9-hydroxy-8-hydroxymethyl-9-o-methoxyphenyl-5-nonenoate§ (3.22 g) in dichloromethane (10 ml), was treated with p-toluenesulphonic acid monohydrate (2.00 g) and the mixture stirred for 96 hours. Ether (50 ml) was added and the mixture washed with 5% w/v sodium bicarbonate (2×20 ml), water (2×20 ml) and saturated brine (20 ml), then dried (MgSO4) and evaporated. The residue was purified by MPLC, eluting with 50% v/v ethyl acetate/hexane to give methyl 5(Z)-7-([2,4,5-cis]-4-o-methoxyphenyl-2[3-pyridylmethyl]-1,3-dioxan-5-yl)heptenoate as a pale yellow oil (1.59 g); NMR (CDCl3): 1.53 (3H, m), 1.80 (3H, m), 2.22 (3H, m), 3.03 (2H, d J=4 Hz), 3.66 (3H, s), 3.80 (3H, s), 3.88 (1H. dm J=11 Hz), 4.00 (1H, bd J=11 Hz), 4.98 (1H, t J=4 Hz), 5.12 (1H, m), 5.18 (1H, d J=2 Hz), 5.30 (1H, m), 6.83 (1H, d J=7 Hz), 6.99 (1H, t J=7 Hz), 7.25 (2H, m), 7.38 (1H, dm J=7 Hz), 7.70 (1H, dm J=7 Hz), 8.48 (1H, dd J=4, 1.5 Hz), 8.60 (1H, d J=1.5 Hz).

[§ This diol ester was previously disclosed in European patent application, publication No. 177121].

(ii) 1M Potassium hydroxide solution (17.6 ml) was added to a stirred solution of methyl 5(Z)-7-([2,4,5-cis]-4-o-methyoxyphenyl-2-[3-pyridylmethyl]-1,3-dioxan-5-yl)heptenoate (1.50 g) in methanol (25 ml). After 3 hours, water (100 ml) was added. The mixture was washed with ether (2×25 ml), then acidified to pH 5 with glacial acetic acid and extracted with further ether (3×50 ml). These extracts were washed with water (2×25 ml) and saturated brine (25 ml), then dried (MgSO$_4$) and evaporated to a small volume. The resulting crystalline solid was collected by filtration to give 5(Z)-7-([2,4,5-cis-]-4-o-methoxyphenyl-2]3-pyridylmethyl]-1,3-dioxan-5-yl)heptenoic acid (1.03 g), mp 119°–120°; NMR (CDCl$_3$): 1.33 (1H, m), 1.68 (3H, m), 1.88 (2H, q J=7 Hz), 2.10 (1H, m), 2.31 (2H, t J=7 Hz), 3.07 (2H, m), 3.80 (3H, s), 3.89 (1H, dm J=11 Hz), 4.00 (1H, dd J=11,1 Hz), 5.03 (2H, m), 5.29 (1H, m), 6.82 (1H, d J=7 Hz), 6.94 (1H, td J=7, 1 Hz), 7.20 (2H, m), 7.36 (1H, m), 7.75 (1H, dt J=7,1 Hz), 8.30 (1H, b), 8.50 (1H, dd J=4,1 Hz), 8.70 (1H, d J=1 Hz); m/e 412 (M+H)$^+$. 2-[3-pyridyl]-1,3-dioxane-5yl)hexenoate (2.29 g) in THF (15 ml). The mixture was heated under reflux for 4 hours, then cooled to ambient temperature when water (100 ml) was added. This mixture was washed with ether (2×25 ml), then acidified to pH 5 with glacial acetic acid and extracted with further ether (3×25 ml). These extracts were washed with water (2×25 ml), saturated brine (25 ml), dried (MgSO$_4$) and evaporated. The residual oil, which crystallized on standing, was recrystallized from ethyl acetate to give 4(Z)-6-([2,4,5-cis]-4-o-hydroxyphenyl-2-[3-pyridyl]-1,3-dioxan-5-yl)hexenoic acid (1.05 g), mp 136°–137° C.; (D$_6$-DMSO): 1.59 (1H, m), 1.99 (1H, m) 2.13 (4H, m) 2.51 (1H, m), 4.11 (2H, m), 5.28 (2H, m), 5.40 (1H, d J=2 Hz), 5.90 (1H, s), 6.80 (2H, m), 7.10 (1H, td J=7, 1.5 Hz), 7.24 (1H, dd J=7, 1 Hz), 7.45 (1H, dd J=7,5 Hz), 7.93 (1H, td J=7,1 Hz), 8.61 (1H, dd J=5, 1.5 Hz), 8.72 (1H, d=1.5 Hz), 9.59 (1H, b); m/e 370 (M+H)$^+$; calculated for C$_{21}$H$_{23}$NO$_5$: C, 68.3; H, 6.3; N, 3.8%; found C, 68.6; H, 6.5; N, 3.6%.

The starting ester was obtained as follows:

(i) A stirred solution of 4(Z)-6-(4-o-hydroxyphenyl-2,2-dimethyl-1,3-dioxan-cis-5-yl)hexenoic acid (§see footnote) (16.0 g) in methanol (50 ml) was treated with a solution of potassium bicarbonate (5.0 g) in water (50 ml). After 15 minutes the solvents were removed in vacuo and the residual gum azeotroped with toluene (4×50 ml) and this residue dried under high vacuum. The resulting froth was dissolved in DMPU (50 ml) an methyl iodide (3.25 ml) added and the mixture stirred for 3 hours. Water (150 ml) was added and the mixture extracted with ether (3×75 ml). These extracts were washed with water (3×40 ml), saturated brine (1×40 ml), dried (MgSO$_4$) and evaporated to give a clear oil (16.85 g). A stirred solution of this oil in dichloromethane (150 ml) was cooled to 4° C. when triethylamine (8.70 ml) was added in one portion followed by the dropwise addition of methanesulphonyl chloride (4.64 ml) over 30 minutes (temperature<10° C.). After the addition, stirring was continued for 1.5 hours at room temperature when water (150 ml) was added and this mixture was extracted with ether (1×200 ml, 2×75 ml). The combined extracts were washed with water (2×50 ml), saturated brine (1×50 ml), dried (MgSO$_4$) and evaporated. The residue was purified by flash chromatography, eluting with 50% v/v ethyl acetate/hexane to give methyl 4(Z)-6-(4-o-methylsulphonyloxyphenyl-2,2-dimethyl-1,3-dioxan-cis-5-yl)hexenoate (A) as a colourless oil (17.86 g); NMR (CDCl$_3$): 1.50 (1H, m), 1.52 (3H, s), 1.55 (3H, s), 1.83 (1H, m), 2.26 (4H, m), 2.50 (1H, m), 3.22 (3H, s), 3.65 (3H, s), 3.79 (1H, dd J=12, 1.5 Hz), 4.16 (1H, dm J=12 Hz), 5.20 (1H, m), 5.35 (1H, m), 5.54 (1H, d J=2 Hz), 7.30 (3H, m), 7.63 (1H, m); m/e 430 (M+NH$_4$)$^+$; calculated for C$_{20}$H$_{28}$O$_7$S: C, 58.2; H, 6.8; S, 7.8%; found C, 57.9; H, 6.8; S, 7.9%. [§ This acid is described in Example 6 of European patent application, Publication No. 201354]

(ii) A stirred solution of A (2.88 g) and 3-pyridinecarboxaldehyde (0.73 ml) in acetonitrile (25 ml) was treated with p-toluenesulphonic acid monohydrate (1.60 g) and the mixture heated at reflux for 5 hours. After cooling, saturated sodium bicarbonate solution (50 ml) was added and the mixture extracted with ether (3×25 ml). These extracts were washed with water (2×25 ml), saturated brine (1×25 ml), dried (MgSO$_4$) and evaporated. The residue was purified by MPLC, eluting with 50% v/v ethyl acetate in hexane to give methyl 4(Z)-6-([2,4,5-cis]-4-o-methylsulphonyloxyphenyl-2-[3-pyridyl]-1,3-dioxan-5-yl)hexenoate as a clear oil (2.29 g); NMR (CDCl$_3$): 1.45 (1H, m), 1.86 (1H, m), 2.11 (4H, m), 2.41 (1H, m) 3.09 (3H, s), 3.46 (3H, s), 3.98 (1H, dm J=11 Hz), 4.08 (1H, dd J=11 1.5 Hz), 5.08 (1H, m), 5.21 (1H, m) 5.38 (1H, dd J=2 Hz), 5.64 (1H, s), 7.18 (4H, m), 7.45 (1H, m), 7.73 (1H, dt J=7, 1.5 Hz), 8.46 (1H, dd J=5, 1.5 Hz), 8.63 (1H, d J=1.5 Hz); m/e (M+H)$^+$.

EXAMPLE 4

Using a similar procedure to that of Example 3, but starting with methyl 4(Z)-6-([2,4,5-cis]-4-o-methylsulphonyloxyphenyl-2-[2-pyridyl]-1,3-dioxan-5-yl)hexenoate there was obtained 4(Z)-6-([2,4,5-cis]-4-o-hydroxyphenyl-2-[2-pyridyl]-1,3-dioxan-5-yl)hexenoic acid in 71% yield as a crystalline solid of mp 165°–165° C.; NMR (D$_6$DMSO): 1.60 (1H, m), 1.98 (1H, m), 2.17 (4H, m), 2.57 (1H, m), 4.05 (1H, bd J=11 Hz), 4.18 (1H, dm J=11 Hz), 5.23 (1H, m), 5.37 (1H, m), 5.40 (1H, d J=2 Hz), 5.77 (1H, s), 6.80 (2H, m), 7.08 (1H, td J=7, 1 Hz), 7.22 (1H, dd J=7,1 Hz), 7.41 (1H, m), 7.72 (1H, d J=7 Hz), 7.90 (1H, td J=7,1 Hz), 8.53 (1H, dm J=5 Hz), 9.54 (1H, s), 11.92 (1H, s); m/e 370 (M+H)$^+$; calculated for C$_{21}$H$_{23}$NO$_5$: C, 68.3; H, 6.3; N, 3.8%; found C, 68.0; H, 6.3; N, 3.7%. The starting ester is prepared in a similar manner to that in Example 3 (ii), but using 2-pyridinecarboxaldehyde in place of 3-pyridinecarboxaldehyde and heating at reflux for 16 hours. Initial purification by MPLC, eluting with 2% v/v methanol in dichloromethane followed by a further purification eluting with ethyl acetate/hexane/acetic acid (50:50:1 v/v) gave methyl 4(Z)-6-([2,4,5-cis]-4-o-methylsulphonyloxyphenyl-2-[2-pyridyl]-1,3-dioxan-5-yl)hexenoate as a clear oil in 27% yield; NMR (CDCl$_3$): 1.68 (1H, m), 2.03 (1H, m), 2.30 (4H, m), 2.51 (1H, m), 3.26 (3H, s), 3.64 (3H, s), 4.20 (1H, dm J=11 Hz), 4.29 (1H, bd J=11 Hz), 5.32 (2H, m), 5.56 (1H, d J=2 Hz), 5.87 (1H, s), 7.35 (4H, m), 7.65 (1H, m), 7.80 (2H, m), 8.53 (1H, m); m/e 462 (M+H)$^+$.

EXAMPLE 5

Using a similar procedure to that in Example 3, but starting with methyl 4(Z)-6-([2,4,5-cis]-4-o-methylsulphonyloxyphenyl-2-[4-pyridyl]-1,3-dioxan-5-yl)hexenoate there was obtained 4(Z)-6-([2,4,5-cis]-4-o-hydroxyphenyl-2-[4-pyridyl]-1,3-dioxan-5-yl)hexenoic acid in 56% yield as a crystalline solid of m.p. 192°–195° C.; NMR (D$_6$-DMSO): 1.57 (1H, m), 1.99 (1H, m), 2.15 (4H, m), 4.07 (1H, bd J=11 Hz), 4.18 (1H, bd J=11 Hz), 5.20 (1H, m), 5.37 (1H, m), 5.41 (1H, d J=2 Hz), 5.86 (1H, s), 6.81 (2H, m), 7.10 (1H, td J=7,1 Hz), 7.25 (1H, bd J=7 Hz), 7.51 (2H, dd J=5, 0.5 Hz), 8.62 (2H, dd J=5, 0.5 Hz), 9.58 (1H, b), 11.93 (1H, b); m/e 370 (M+H)$^+$; calculated for C$_{21}$H$_{23}$NO$_5$: C, 68.3; H, 6.3;

N, 3.8%; found C, 68.2; H, 6.3; N, 3.7%. The starting ester is prepared in a similar manner to that in Example 3 (ii), but using 4-pyridinecarboxaldehyde in place of 3-pyridinecarboxaldehyde and heating at reflux for 16 hours. Initial purification by MPLC, eluting with 1% v/v acetic acid in ethyl acetate followed by a further purification eluting with 2% v/v methanol in dichloromethane gave methyl 4(Z)-6-([2,4,5-cis]-4-o-methylsulphonyloxyphenyl-2-[4-pyridyl]-1,3-dioxane-5-yl)hexenoate as a clear oil in 32% yield; NMR (CDCl$_3$): 1.61 (1H, m), 2.05 (1H, m) 2.28 (4H, m), 2.55 (1H, m), 3.29 (3H, s), 3.63 (3H, s), 4.16 (1H, bd J=11 Hz), 4.27 (1H, bd J=11 Hz), 5.23 (1H, m), 5.40 (1H, m), 5.56 (1H, d J=2 Hz), 5.78 (1H, s), 7.37 (3H, m), 7.52 (2H, bd J=5 Hz), 7.63 (1H, m), 8.69 (2H, bd J=5 Hz); m/e 462 (M+H)+.

EXAMPLE 6

Using a similar procedure to that described in Example 1, but starting with 5(Z)-7-([2,4,5-cis]-4-o-methoxyphenyl-2-[3-pyridyl]-1,3-dioxan-5-yl)heptenoic acid instead of 4(Z)-6-([2,4,5-cis]-4-o-methoxyphenyl-2-[3-pyridyl]-1,3-dioxan-5-yl)hexenoic acid, there was obtained after flash chromatography, eluting with 1% v/v acetic acid in ethyl acetate, and a further purification by MPLC, eluting with ethyl acetate/hexane/acetic acid (80:20:1 v/v), 5(Z)-7-([2,4,5-cis]-4-o-hydroxyphenyl-2-[3-pyridyl]-1,3-dioxan-5-yl)heptenoic acid (1 mole acetic acid adduct) as a pale yellow oil (83%); NMR (CDCl$_3$): 1.68 (2H, m), 1.86 (2H, m), 2.08 (2H, m), 2.09 (3H, s), 2.32 (2H, t J=7 Hz), 2.73 (1H, m), 4.14 (1H, dm J=11 Hz), 4.31 (1H, dd J=11,1 Hz), 5.30 (1H, m), 5.47 (1H, m), 5.49 (1H, d J=2 Hz), 5.81 (1H,s), 6.87 (2H, m), 7.15 (2H, m), 7.44 (1H, m), 7.96 (1H, dt J=7,1 Hz), 8.65 (1H, dd J=5,1 Hz), 8.95 (1H, d J=1 Hz); m/e 384 (M+H)+; calculated for C$_{22}$H$_{25}$NO$_5$, CH$_3$COOH: C, 65.0; H, 6.6; N, 3.2%; found: C, 65.2; H, 6.7; N, 3.1%.

The starting material was obtained as follows:

(1) 3-Pyridinecarboxaldehyde (1.07 g) was added to a stirred suspension of p-toluenesulphonic acid monohydrate (2.10 g) in dichloromethane (15 ml). Methyl 5(Z)-erythro-9-hydroxy-8-hydroxymethyl-9-o-methoxyphenyl-5-nonenoate (3.22 g) in dichloromethane (2 ml) was added and stirring continued for 72 hours. Ether (50 ml) was then added and the mixture washed with 5% w/v sodium bicarbonate (3×25 ml), water (25 ml) and saturated brine (25 ml), then dried (MgSO$_4$) and evaporated. The residue was purified by MPLC, eluting with 50% v/v ethyl acetate in hexane, to give methyl 5(Z)-7-([2,4,5-cis]-4-o-methoxyphenyl-2-[3-pyridyl]-1,3-dioxan-5-yl)heptenoate as an oil (1.41 g); NMR (CDCl$_3$): 1.62 (3H, m), 1.98 (3H, m), 2.21 (2H, t J=7 Hz), 2.52 (1H, m), 3.63 (3H, s), 3.85 (3H, s), 4.15 (1H, dm J=11 Hz), 4.23 (1H, dd J=11,1 Hz), 5.30 (2H, m), 5.45 (1H, d J=2 Hz), 5.81 (1H, s), 6.88 (1H, d J=7 Hz), 6.98 (1H, t J=7 Hz), 7.27 (1H, t J=7,1 Hz), 7.36 (1H, m), 7.47 (1H, bd J=7 Hz), 7.92 (1H, dm J=7 Hz) 8.62 (1H, dd J=4,1 Hz), 8.81 (1H, bs).

(ii) 1M Potassium hydroxide solution (17 ml) was added to stirred solution of methyl 5(Z)-7-([2,4,5-cis]-4-o-methoxyphenyl-2-[3-pyridyl]-1,3-dioxan-5-yl)heptenoate in methanol (25 ml). After 1.5 hours, water (100 ml) was added. The mixture was washed with ether (3×25 ml), then acidified to pH 5 with glacial acetic acid and extracted with further ether (2×50 ml). These extracts were washed with saturated brine (25 ml), dried (MgSO$_4$) and evaporated. The residue, on trituration with ether, gave a white solid which, after recrystallisation from ether/hexane gave 5(Z)-7-([2,4,5-cis]-4-o-methoxyphenyl-2-[3-pyridyl]-1,3-dioxan-5-yl)heptenoic acid (800 mg) of m.p. 104°-106° C.; NMR (CDCl$_3$): 1.67 (3H, m), 2.02 (3H, m), 2.30 (2H, t J=7 Hz), 2.60 (1H, m), 3.87 (3H, s), 4.13 (1H, dm J=11 Hz), 4.25 (1H, d J=11 Hz), 5.23 (1H, m), 5.40 (1H, m), 5.47 (1H, d J=2 Hz), 5.82 (1H, s), 6.88 (1H, d J=7 Hz), 6.98 (1H, t J=Hz), 7.27 (1H, td J=7,1.5 Hz), 7.38 (1H, m), 7.45 (1H, bd J=7 Hz), 7.92 (1H, dm J=7 Hz), 8.16 (1H, b), 8.61 (1H, dm J=4 Hz), 8.88 (1H, bs); m/e: 398 (M+H)+.

EXAMPLE 7

Using a similar procedure to that described in Example 3, but starting with methyl-5(Z)-7-([2,4,5-cis]-4-o-methylsulphonyloxyphenyl-2-[4-pyridyl]-1,3-dioxan-5-yl)heptenoate there was obtained 5(Z)-7-([2,4,5-cis]-4-o-hydroxyphenyl-2-[4-pyridyl]-1,3-dioxan-5-yl)heptenoic acid in 83% yield as a crystalline solid of m.p. 167°-169° C.; NMR (D$_6$-DMSO): 1.49 (2H, q J=7 Hz), 1.57 (1H, m), 1.89 (2H, q J=7 Hz), 1.97 (1H, m), 2.10 (2H, t J=7 Hz), 2.41 (1H, m), 4.06 (1H, bd J=11 Hz), 4.17 (1H, bd J=11 Hz), 5.28 (2H, m), 5.41 (1H, d J=2 Hz), 5.83 (1H, s), 6.79 (2H, m), 7.08 (1H, td J=7,2 Hz), 7.24 (1H, d J=7 Hz), 7.50 (2H, bd J=5 Hz), 8.63 (2H, bd J=5 Hz), 9.57 (1H, b), 11.89 (1H, b); m/e 384 (M+H)+; calculated for C$_{22}$H$_{25}$NO$_5$: C, 68.9, H, 6.5; N, 3.65%; found C, 68.7; H, 6.6; N, 3.4%.

The starting material was prepared in a similar manner to that in Example 3 (i) starting from 5(Z)-7-(4-o-hydroxyphenyl-2,2-dimethyl-1,3-dioxan-cis-5-yl)heptenoic acid instead of 4(Z)-6-(4-o-hydroxyphenyl-2,2-dimethyl-1,3-dioxan-cis-5-yl)hexenoic acid. There was thus obtained after flash chromatography, eluting with 35% v/v ethyl acetate in hexane, methyl 5(Z)-7-(4-o-methylsulphonyloxyphenyl-2,2-dimethyl-1,3-dioxan-cis-5-yl)heptenoate (A) as a colourless oil (94%); NMR (CDCl$_3$): 1.52 (3H, s), 1.53 (1H, m), 1.54 (3H, s), 1.63 (2H, q J=7 Hz), 1.80 (1H, m), 1.97 (2H, q J=7 Hz), 2.23 (2H, t J=7 Hz), 2.45 (1H, m), 3.22 (3H, s), 3.66 (3H, s), 3.78 (1H, dd J=11,1.5 Hz), 4.13 (1H, dm J=11 Hz), 5.19 (1H, m), 5.31 (1H, m), 5.54 (1H, d J=2 Hz), 7.29 (3H, m), 7.63 (1H, m); m/e 427 (M+H)+. Oil A was then reacted with 4-pyridinecarboxaldehyde using a similar procedure to that described in Example 3 (ii), to give after MPLC, eluting with 70% v/v ethyl acetate in hexane, methyl 5(Z)-7-([2,4,5-cis]-4-o-methylsulphonyloxyphenyl-2-[4-pyridyl]-1,3-dioxan-5-yl)heptenoate as a clear oil (33%); NMR (CDCl$_3$): 1.61 (3H, m), 1.99 (3H, m), 2.23 (2H, t J=7 Hz), 2.50 (1H, m), 3.28 (3H, s), 3.63 (3H, s), 4.16 (1H, dm J=11 Hz), 4.28 (1H, dd J=11,1 Hz), 5.21 (1H, m), 5.38 (1H, m), 5.56 (1H, d J=2 Hz), 5.77 (1H, s), 7.37 (3H, m), 7.56 (2H, bd J=5 Hz), 7.63 (1H, m), 8.69 (2H, bd J=5 Hz); m/e 476 (M+H)+.

EXAMPLE 8

A stirred solution of methyl 6(Z)-8-(4-o-methylsulphonyloxyphenyl-2,2-dimethyl-1,3-dioxane-cis-5yl)octenoate (C) (2.20 g) and 3-pyridinecarboxaldehyde (0.52 ml) in acetonitrile (10 ml) was treated with p-toluenesulphonic acid monohydrate (1.14 g) and the mixture was heated at reflux for 5 hours. The cooled solution was added to 5% w/v sodium bicarbonate solution (50 ml) and this mixture extracted with ether (3×20 ml). The combined extracts were washed with water (2×20 ml), saturated brine (20 ml), dried (MgSO$_4$) and evaporated. The residue was partially purified by MPLC, eluting with ethyl acetate/hexane (9:1 v/v) to give methyl 6(Z)-8-([2,4,5-cis]-4-o-methylsulphonyloxyphenyl-2-[3-pyridyl]-1,3-dioxan-5-yl)octenoate an oil (2.00 g). This oil was dissolved in methanol (30 ml) and 2M sodium hydroxide (21 ml) added and the mixture was heated at reflux for 2 hours. Water (50 ml) was added and the mixture washed with ether (3×20 ml). Acidified to pH 5 with glacial acetic acid and extracted with ether (3×20 ml). These combined extracts were washed with water (2×20 ml), saturated brine (20 ml), dried (MgSO$_4$) and evaporated. Purification by MPLC, eluting ethyl acetate/hexane/acetic acid (70:30:1 v/v) gave 6(Z)-8-([2,4,5-cis]-4-o-hydroxyphenyl-2-[3-pyridyl]-1,3-dioxan-5-yl)octenoic acid (1 mole acetic acid adduct) (1.20 g) as an oil; NMR (D$_6$-DMSO): 1.23 (2H, m), 1.40 (2H, m), 1.60 (1H, m), 1.91 (5H, m), 2.12 (2H, t J=7 Hz), 2.46 (1H, m), 4.07 (1H, bd J=11 Hz), 4.18 (1H, bd J=11 Hz), 5.30 (2H, m), 5.41 (1H, d J=2 Hz), 5.90 (1H, s), 6.81 (2H, m), 7.10 (1H, m), 7.26 (1H, dd J=7,1 Hz), 7.46 (1H, m), 7.92 (1H, dt J=7,1 Hz), 8.6 (1H, dd J=5,1 Hz), 8.72 (1H, d J=1 Hz); m/e 398 (M+H)$^+$; calculated for C$_{23}$H$_{27}$NO$_5$, CH$_3$OOH: C, 65.6; H, 6.8; N, 3.1%; found: C, 66.0; H, 6.7; N, 3.3%.

The starting material C was prepared as follows:

(i) Solid potassium t-butoxide (33.6 g) was added under argon to a stirred, ice-cooled mixture of (5-carboxypentyl) triphenylphosphonium bromide (51.4 g) and [2,3-trans]-tetrahydro-5-hydroxy-3-hydroxymethyl-2-o-methoxyphenylfuran §(16.8 g) in dry THF (450 ml). The mixture was stirred for 1 hour at 4° C., then for 1 hour at ambient temperature and was then poured into ice-water (1 l). The mixture obtained was washed with ether (2×300 ml) to remove the bulk of the neutral material. The aqueous phase was acidified to pH 4 with 1M hydrochloric acid and extracted with ether (3×400 ml). These combined extracts were washed with water (3×200 ml), saturated brine (1×200 ml), dried (MgSO$_4$) and evaporated. The residue was purified by flash chromatography, eluting with ethyl acetate/hexane/acetic acid (80:20:1 v/v) to give a colourless oil. A solution of this oil in 2,2-dimethoxypropane (75 ml) was treated with p-toluenesulphonic acid monohydrate (20 mg) and the mixture stirred for 1 hour. Ether (500 ml) was added and this mixture extracted with 0.5M sodium hydroxide (1×200 ml, 1×50 ml). The aqueous extracts were acidified to pH 5 with glacial acetic acid and extracted with ether (1×300 ml, 2×150 ml). These organic extracts were washed with water (2×150 ml), saturated brine (1×150 ml), dried (MgSO$_4$) and evaporated. Flash chromatography of the residual oil, eluting with toluene/ethyl acetate/acetic acid (85:15:2 v/v) followed by a crystallisation from hexane gave 6(Z)-8-(4-o-methoxyphenyl-2,2-dimethyl-1,3-dioxan-cis-5-yl)octenoic acid (A) (23.8 g) of m.p. 77°-79° C.; NMR (CDCl$_3$): 1.36 (2H, q J=7 Hz), 1.57 (9H, m), 1.78 (1H, m), 1.95 (2H, m), 2.31 (2H, t J=7 Hz), 2.47 (1H, m), 3.78 (1H, dd J=11,1 Hz), 4.16 (2H, dm J=11 Hz), 5.23 (2H, m), 5.44 (1H, d J=2 Hz), 6.82 (1H, dd J=7,1 Hz), 6.97 (1H, td J=7,1 Hz), 7.22 (1H, td J=7,1.5 Hz), 7.47 (1H, dd J=7,1.5 Hz); m/e 363 (M+H)$^+$. [§Disclosed in European patent application, Publication No. 142323].

(ii) A stirred solution of lithium diphenylphosphide [prepared from chlorodiphenylphosphine (60 ml) and lithium metal (5.8 g) in dry THF (250 ml)] was treated at 4° C. under argon with a solution of A (24.26 g) in dry THF (30 ml). The mixture was stirred for 15 minutes at 4° C., then for 16 hours at 50° C., cooled to 10° C. and added to ice water (800 ml). The aqueous solution was washed with ether (2×300 ml), acidified to pH 5 with glacial acetic acid and extracted with ether (3×300 ml). These extracts washed with water (2×150 ml), saturated brine (1×150 ml), dried (MgSO$_4$) and evaporated. The residue was purified by flash chromatography, eluting with ethyl acetate/hexane/acetic acid (25:75:1 v/v), to give 6(Z)-8-(4-o-hydroxyphenyl-2,2-dimethyl-1,3-dioxan-cis-5-yl)octenoic acid (B) as a colourless oil (22.0 g); NMR (CDCl$_3$): 1.37 (2H, q J=7 Hz), 1.60 (9H, m), 1.83 (1H, m), 1.97 (2H, q J=7 Hz), 2.32 (2H, t J=7 Hz), 2.67 (1H, m), 3.85 (1H, dd J=11,1.5 Hz), 4.13 (1H, dm J=11 Hz), 5.21 (1H, m), 5.41 (1H, m), 5.45 (1H, d J=2 Hz), 6.87 (3H, m), 7.18 (1H, m), 8.50 (1H, b); m/e 366 (M+NH$_4$)$^+$.

(iii) In a similar manner to that in example 3 (i), but starting from the acid B above, there was obtained after flash chromatography, eluting, with 35% v/v ethyl acetate in hexane, methyl 6(Z)-8-(4-o-methanesulphonyloxyphenyl-2,2-dimethyl-1,3-dioxan-cis-5-yl)octenoate (C) as a colourless oil (97%); NMR (CDCl$_3$): 1.32 (2H, q J=7 Hz), 1.54 (9H, m), 1.79 (1H, m), 1.93 (2H, q J=7 Hz), 2.27 (2H, t J=7 Hz), 2.47 (1H, m), 3.22 (3H, s), 3.67 (3H, s), 3.79 (1H, dd J=11,1 Hz), 4.14 (1H, dm J=11 Hz), 5.15 (1H, m), 5.36 (1H, m), 5.53 (1H, d J=2 Hz), 7.31 (3H, m), 7.62 (1H, m); m/e 441 (M+H)$^+$.

EXAMPLE 9

Using a similar procedure to that described in Example 8, but starting from 4-pyridinecarboxaldehyde and heating under reflux for 16 hours there was obtained after MPLC, eluting with ethyl acetate/hexane (7:3 v/v) methyl 6(Z)-8-([2,4,5-cis]-4-o-methylsulphonyloxyphenyl-2-[4-pyridyl]-1,3-dioxan-5-yl)octenoate, as an oil (0.91 g). The oil was dissolved in THF (5 ml) and 2M sodium hydroxide (9 ml) added and the mixture was heated, with vigorous stirring, for 5 hours at 65° C. Water (50 ml) was added and the mixture washed with ether (2×20 ml). Acidified to pH5 with glacial acetic acid and extracted with ether (1×40 ml, 2×20 ml). The combined extracts were washed with water (2×20 ml), saturated brine (1×20 ml), dried (MgSO$_4$) and evaporated. Crystallisation from ethyl acetate gave 6(Z)-8-([2,4,5-cis]-4-o-hydroxyphenyl-2-[4-pyridyl]-1,3-dioxan-5-yl)octenoic acid (0.45 g), m.p. 171°-171° C.; NMR (D$_6$-DMSO): 1.23 (2H, m), 1.41 (2H, m) 1.58 (1H, m), 1.87 (2H, q J=7 Hz), 1.98 (1H, m), 2.13 (2H, t J=7 Hz), 2.42 (1H, m), 4.08 (1H, bd J=11 Hz), 4.18 (1H, bd J=11 Hz), 5.29 (2H, m), 5.42 (1H, d J=2 Hz), 5.86 (1H, s), 6.81 (2H, m), 7.10 (1H, td J=7,1.5 Hz), 7.28 (1H, bd J=7 Hz), 7.51 (2H, dd J=5,0.5 Hz), 8.63 (2H, dd J=5,0.5 Hz), 9.6 (1H, b); m/e 398 (M+H)$^+$; calculated for C$_{23}$H$_{27}$NO$_5$: C, 69.5; H, 6.8; N, 3.5%; found C, 69.2; H, 6.9, N, 3.5%.

EXAMPLE 10

A solution of 3-pyridinecarboxaldehyde (0.802 g) and 4(Z)-6-(4-phenyl-2,2-dimethyl-1,3-dioxan-cis-5-yl)hexenoic acid (1.52 g) in acetonitrile (10 ml) was treated with p-toluenesulphonic acid monohydrate (1.56 g) and the stirred mixture heated at reflux for 3 hours and then stirred overnight at ambient temperature. Water (50 ml) was added and the solution basified to pH 10-11 with 2M sodium hydroxide. The resulting solution was washed with ether (2×25 ml), acidified to pH 5 with glacial acetic acid and extracted with ether (3×25 ml). The extracts were washed with water (2×30 ml), dried (MgSO$_4$) and evaporated. The residue was purified by MPLC, eluting with ethyl acetate/hexane/acetic acid (70:30:1 v/v), to give a clear oil which crystallised on standing. Recrystallisation from ethyl acetate/hexane (1:1 v/v) gave 4(Z)-6-([2,4,5-cis]-4-phenyl-2-[3-pyridyl]-1,3-dioxan-5-yl)hexenoic acid (830 mg), m.p. 118°–120° C.; NMR (CDCl$_3$): 1.72 (2H, m) 2.31 (4H, m), 2.60 (1H, m), 4.14 (1H, dm J=11 Hz), 4.30 (1H, dd J=11,1 Hz), 5.25 (1H, d J=2 Hz), 5.27 (1H, m), 5.47 (1H, m), 5.80 (1H, s), 7.33 (6H, m), 8.00 (1H, dt J=7,1.5 Hz), 8.61 (1H, dd J=5,1.5 Hz), 8.84 (1H, d J=1.5 Hz), 9.53 (1H, b); m/e 354 (M+H)$^+$; calculated for C$_{21}$H$_{23}$NO$_4$: C, 71.4; H, 6.6, N, 4.0%; found: C, 71.3, H, 6.4; N, 3.9%. The starting material was obtained as follows:

Solid potassium t-butoxide (8.85 g) was added under argon to a stirred, ice-cooled mixture of (3-carboxypropyl)triphenylphosphonium bromide (16.94 g) and (4-phenyl-2,2-dimethyl-1,3-dioxan-cis-5-yl)acetaldehyde (5.28 g) in THF (200 ml). The mixture was stirred for 15 minutes at 4° C., then for 4 hours at ambient temperature and was then poured into water (200 ml). The mixture obtained was washed with ether (3×50 ml) to remove the bulk of neutral material. The aqueous phase was acidified to pH 5 with glacial acetic acid and extracted with ether (3×100 ml). These extracts were washed with water (2×30 ml), saturated brine (50 ml), dried (MgSO$_4$) and evaporated. The residue was purified by MPLC, eluting with ethyl acetic/hexane/acetic acid (30:70:1 v/v) to give 4(Z)-6-(4-phenyl-2,2-dimethyl-1,3-dioxancis-5-yl)hexenoic acid as a colourless oil (5.22 g); NMR (CDCl$_3$): 1.52 (6H, s), 1.57 (2H, m), 2.30 (4H, m), 2.50 (1H, m), 3.81 (1H, dd J=11,1 Hz), 4.13 (1H, dm J=11 Hz), 5.21 (1H, d J=2 Hz), 5.23 (1H, m) 5.39 (1H, m), 7.30 (5H, m);m/e 305 (M+H)$^+$.

EXAMPLES 11–13

Using a similar procedure to that described in Example 3, but starting from the appropriate methyl 4(Z)-6-([2,4,5-cis]-4-o-methylsulphonyloxyphenyl-2-[pyridylmethyl]-1,3-dioxan-5-hexenoate, there were prepared:

EXAMPLE 11

4(Z)-6-([2,4,5-cis]-4-o-hydroxyphenyl-2-[2-pyridylmethyl]-1,3-dioxan-5-yl)hexenoic acid in 87% yield after recrystallisation from ethanol/hexane, m.p. 165°–166° C.; NMR (D$_6$-DMSO): 1.47 (1H, m), 1.84 (1H, m), 2.11 (4H, m), 2.34 (1H, m), 3.10 (2H, d J=5 Hz), 3.88 (2H, bs), 5.16 (3H, m), 5.31 (1H, m), 6.79 (2H, m), 7.06 (1H, td J=7,1 Hz), 7.20 (2H, m), 7.37 (1H, d J=7 Hz), 7.69 (1H, td J=7,1.5 Hz), 8.48 (1H, dt J=5, 0.5 Hz), 9.43 (1H, b); m/e 384 (M+H)$^+$; calculated for C$_{22}$H$_{25}$NO$_5$: C, 68.9; H, 6.5; N, 3.6%; found: C, 69.2; H, 6.5; N, 3.4%.

EXAMPLE 12

4(Z)-6-([2,4,5-cis]-4-o-hydroxyphenyl-2-[3-pyridylmethyl]-1,3-dioxan-5-yl)hexenoic acid in 77% yield, after recrystallisation from ethyl acetate, m.p. 130°–132° C.; NMR (D$_6$-DMSO): 1.38 (1H, m), 1.81 (1H, m), 2.12 (5H, m), 3.00 (2H, d J=5 Hz), 3.90 (1H, bs), 5.09 (3H, m), 5.30 (1H, m), 6.80 (2H, m), 7.08 (1H, td J=7,1 Hz), 7.20 (1H, bd J=7 Hz), 7.31 (1H, m), 7.73 (1H, dt J=7, 0.5 Hz), 8.91 (1H, dd J=5,1 Hz), 8.52 (1H, bs), 9.47 (1H, b), 11.97 (1H, b); m/e 384 (M+H)$^+$; calculated for C$_{22}$H$_{25}$NO$_5$: C, 68.9; H, 6.5; N, 3.6%; found: C, 68.7; H, 6.6; N, 3.6%.

EXAMPLE 13

4(Z)-6-([2,4,5-cis]-4-o-hydroxyphenyl-2-[4-pyridylmethyl]-1,3-dioxan-5-yl)hexenoic acid in 87% yield, after recrystallisation from ethanol/hexane, m.p. 165°–166° C.; NMR (D$_6$-DMSO): 1.39 (1H, m), 1.81 (1H, m), 2.13 (5H, m), 2.99 (2H, d J=5 Hz), 3.88 (2H, bs), 5.10 (3H, m), 5.30 (1H, m), 6.80 (2H, m), 7.07 (1H, td J=7,1 Hz), 7.18 (1H, bd J=7 Hz), 7.34 (2H, dd J=5, 0.5 Hz), 8.46 (2H, bd J=5 Hz), 9.47 (1H, s), 11.90 (1H, b); m/e 398 (M+H)$^+$; calculated for C$_{22}$H$_{25}$NO$_5$: C, 68.9; H, 6.5; N, 3.6%; found: C, 68.8, H, 6.6; N, 3.5%.

The starting materials were prepared as follows:

(i) (for Example 11): Potassium t-butoxide (8.40 g) was added under argon to a stirred, ice-cooled, mixture of 2-pyridinecarboxaldehyde (5.36 g) and (methoxymethyl)triphenylphosphonium chloride (25.65 g) in dry THF (100 ml). The mixture was stirred for 1 hour and was then poured into ice-water (100 ml). The mixture was extracted with ether (3×50 ml) and the organic solution extracted with 2M hydrochloric acid (3×25 ml). These acid extracts were washed with ether (25 ml), basified to pH 11 with 2M sodium hydroxide and extracted with ether (1×100 ml). These combined extracts were washed with water (25 ml), saturated brine (2×25 ml), dried (MgSO$_4$) and evaporated. Flash chromatography, eluting with ether, gave 1-methoxy-2-(2-pyridyl)ethene as a yellow oil (4.03 g). A solution of this oil (810 mg) and methyl 4(Z)-6-(4-o-methylsulphonyloxyphenyl-2,2-dimethyl-1,3-dioxan-cis-5-yl)hexenoate (1.65 g) in acetonitrile (10 ml) was treated with p-toluenesulphonic acid monohydrate (1.25 g) and the mixture stirred at 80° C. for 18 hours. Ether (100 ml) was added to the cooled solution and the mixture washed with 5% w/v sodium bicarbonate (1×40 ml), saturated brine (2×25 ml), dried (MgSO$_4$) and evaporated. Purification of the residue by MPLC, eluting with ethyl acetate/hexane (75:25) gave methyl 4(Z)-6-([2,4,5-cis]-4-o-methylsulphonyloxyphenyl-2-[2-pyridylmethyl]-1,3-dioxan-5-yl)hexenoate as a pale yellow oil (1.50 g); NMR (CDCl$_3$): 1.51 (1H, m), 1.88 (1H, m), 2.25 (4H, m), 2.41 (1H, m), 3.22 (3H, s), 3.29 (2H, d J=5 Hz), 3.68 (3H, s), 3.91 (1H, dm J=11 Hz), 4.06 (1H, bd J=11 Hz), 5.26 (4H, m), 7.15 (1H, m), 7.32 (4H, m), 7.60 (2H, m), 8.56 (1H, dd J=5, 0.5 Hz); m/e 476 (M+H)$^+$.

(ii) In a similar manner, but starting from the appropriate pyridinecarboxaldehyde, there were prepared:

(a) starting material for Example 12: methyl 4(Z)-6([2,4,5-cis]-4-o-methylsulphonyloxyphenyl-2-[3-pyridylmethyl]-1,3-dioxan-5-yl)hexenoate as a pale yellow oil (75%) (which could be crystallised from ethyl acetate/hexane to give a solid, mp 85°–86° C.). NMR (CDCl$_3$): 1.40 (1H, m), 1.82 (1H, m), 2.20 (5H, m), 3.50 (2H, d J=5 Hz), 3.21 (3H, s), 3.67 (3H, s), 3.88 (1H, dm J=11 Hz), 4.03 (1H, dd J=11,1 Hz), 5.00 (1H, t J=5 Hz), 5.12 (1H, m), 5.26 (1H, d J=2 Hz), 5.30 (1H, m), 7.29 (4H, m), 7.52 (1H, m), 7.68 (1H, dt J=7,1.5 Hz), 8.49 (1H, dd J=5,1 Hz), 8.58 (1H, d J=1.5 Hz); m/e 476 (M+H)$^+$.

(b) starting material of Example 13: methyl 4(Z)-6([2,4,5-cis]-4-o-methylsulphonyloxyphenyl-2-[4-pyridylmethyl]-1,3-dioxan-5-yl)hexenoate as a pale yellow oil (85%); NMR (CDCl$_3$): 1.43 (1H, m), 1.85 (1H, m), 2.22 (5H, m), 3.06 (2H, d J=5 Hz), 3.22 (3H, s), 3.67 (3H, s), 3,.89 (1H, dm J=11 Hz), 4.03 (1H, dd J=11,1 Hz), 5.03 (1H, t J=5), 5.13 (1H, m), 5.29 (1H, d J=2 Hz), 5.32 (1H, m), 7.31 (5H, m), 7.50 (1H, m), 8.53 (2H, dd J=5, 1 Hz); m/e 476 (M+H)$^+$.

EXAMPLE 14

Using a similar procedure to that described in Example 1, but starting from ethane thiol (0.85 ml), sodium hydride (0.55 g; 50% w/w dispersion in mineral oil), DMPU (15 ml) and 5(Z)-7-([2,4,5-cis]-4-o-methoxyphenyl-2-[4-pyridylmethyl]-1,3-dioxan-5-yl)heptenoic acid (0.81 g), there was obtained after flash chromatography using dichloromethane/methanol/acetic acid (95:5:1 v/v) as eluant, 5(Z)-7-([2,4,5-cis]-4-o-hydroxyphenyl-2-[4-pyridylmethyl]-1,3-dioxan-5-yl)heptenoic acid, as a white solid (163 mg, after recrystallisation from ethyl acetate), m.p. 185°-187° C.; NMR (D6-DMSO): 1.42 (3H, m), 1.80 (3H, m), 2.11 (2H, t J=7 Hz), 2.20 (1H, m), 2.98 (2H, d J=4 Hz), 3.88 (2H, bs), 5.06 (1H, t J=4 Hz), 5.10 (1H, m), 5.13 (1H, d J=2 Hz), 5.28 (1H, m), 6.79 (2H, m), 7.07 (1H, td J=7, 1.5 Hz), 7.19 (1H, d J=7 Hz), 7.33 (2H, d J=5 Hz), 8.46 (2H, d J=5 Hz); m/e 398 (M+H)+; calculated for $C_{23}H_{27}NO_5$: C, 69.5; H, 6.8; N, 3.5%; found: C, 69.2; H, 6.9; N, 3.2%.

The starting acid was prepared as follows:

A mixture of 1-methoxy-2-(4-pyridyl)ethene (obtained as an oil using an analogous procedure to that described above for 1-methoxy-2-(2-pyridyl)ethene but starting from 4-pyridinecarboxaldehyde) (1.35 g) and 5(Z)-erythro-9-hydroxy-8-hydroxymethyl-9-o-methoxyphenyl-5-nonenoic acid (1.54g) in acetontrile (15 ml) was treated with concentrated hydrochloric acid (26% w/v; 1.34 ml) and the mixture stirred for 48 hours. Sodium hydroxide solution (0.25M, 50 ml) was then added and the mixture washed with ether (2×20 ml). The aqueous phase was acidified to pH 5 with glacial acetic acid and extracted with ether (2×40 ml). These combined extracts were washed with water (4×15 ml), dried (MgSO4) and evaporated. Purification of the residue by flash chromatography using 1% v/v acetic acid in ethyl acetate gave, after recrystallisation from ethyl acetate/hexane, 5(Z)-7-([2,4,5-cis]-4-o-methoxyphenyl-2-[4-pyridylmethyl]-1,3-dioxan-5-yl)heptenoic acid as a white solid (0.51 g), m.p. 143°-145° C.; NMR (D6-DMSO): 1.40 (3H, m), 1.75 (3H, m), 2.08 (2H, t J=7 Hz), 2.18 (1H, m), 2.99 (2H, d J=4 Hz), 3.77 (3H, s), 3.88 (2H, bs), 5.07 (1H, t J=4 Hz), 5.10 (1H, m), 5.16 (1H, d J=2 Hz), 5.26 (1H, m), 6.97 (2H, m), 7.25 (2H, m), 7.33 (2H, dd J=5, 0.5 Hz), 8.47 (2H, dd J=5, 0.5 Hz), 11.98 (1H, b); m/e 412 (M+H)+.

EXAMPLE 15

A stirred solution of the 1-methoxy-2-(3-pyridyl)ethene (obtained as an oil using an analogous procedure to that described in Example 11 for 1-methoxy-2-(2-pyridyl)ethene but starting from 3-pyridinecarboxaldehyde) (229 mg) and 4(Z)-6-(4-phenyl-2,2-dimethyl-1,3-dioxan-cis-5-yl)-hexenoic acid (344 mg) in acetonitrile (5 ml) was treated with p-toluenesulphonic acid monohydrate (342 mg) and the mixture heated under reflux for 3 hours. The mixture was then cooled to ambient temperature, 1M sodium hydroxide (10 ml) added and stirring was continued for a further 30 minutes. Water (50 ml) was added, the solution washed with ether (2×20 ml), acidified to pH 5 with glacial acetic acid and extracted with ether (3×25 ml). These extracts were washed with water (2×25 ml), saturated brine (25 ml), dried (MgSO4) and evaporated. The residual oil was purified by MPLC, eluting with ethyl acetate/hexane/acetic acid (80:20:1 v/v), to give 4(Z)-6-([2,4,5-cis]-4-phenyl-2-[3-pyridylmethyl]-1,3-dioxan-5-yl)hexenoic acid (1.66 mole adduct with acetic acid) as a clear oil (220 mg); NMR (CDCl3): 1.42 (1H, m), 1.59 (1H, m), 2.10 (5H, s), 2.20 (5H, m), 3.08 (2H, d J=4 Hz), 3.86 (1H, dm J=11 Hz), 4.04 (1H, dd J=11, 1 Hz), 4.98 (2H, m), 5.11 (1H, m), 5.39 (1H, m), 7.29 (6H, m), 7.73 (2.7H, b), 7.80 (1H, dt J=7, 1 Hz), 8.48 (1H, dd J=4, 1 Hz), 8.61 (1H, d J=1.5 Hz); m/e 368 (M+H)+; calculated for $C_{22}H_{25}NO_4$. 1.66 $CH_3COOH$: C, 65.1; H, 6.8; N, 3.0%; found: C, 65.0; H, 6.9; N, 3.0%.

EXAMPLE 16

Using a similar procedure to that described in Example 15, but starting from 5(Z)-7-(4-phenyl-2,2-dimethyl-1,3-dioxan-cis-5-yl)heptenoic acid, there was obtained after flash chromatography using 1% v/v acetic acid in ethyl acetate as eluant, 5(Z)-7-(4-phenyl-2-[3-pyridylmethyl]-1,3-dioxan-5-yl)heptenoic acid as a white solid (9%, after recrystallisation from ethyl acetate), m.p. 119°-120° C.; NMR (CDCl3): 1.34 (1H, m), 1.60 (3H, m), 1.88 (2H, q J=7 Hz), 2.09 (1H, m), 2.31 (2H, t J=7 Hz), 3.09 (2H, m), 3.88 (1H, dm J=11 Hz), 4.04 (1H, dd J=11, 1 Hz), 4.99 (1H, d J=2 Hz), 5.02 (1H, t J=4 Hz), 5.04 (1H, m), 5.34 (1H, m), 6.70 (1H, b), 7.26 (6H, m). 7.74 (1H, dt, J=7, 1 Hz), 8.50 (1H, dd J=5, 1 Hz), 8.70 (1H, d J=1.5 Hz); m/e 382 (M+H)+; calculated for $C_{23}H_{27}NO_4$: C, 72.4; H, 7.1; N, 3.7%; found C, 72.4; H, 7.1; N, 3.7%.

EXAMPLE 17

A solution of methyl 4(Z)-6-(4-o-methylsulphonyloxyphenyl-2,2-dimethyl-1,3-dioxan-cis-5-yl)hexenoate (1.80 g) and 2-methyl-2-(3-pyridyl)propionaldehyde (0.81 g) in acetonitrile (6 ml) was treated with p-toluenesulphonic acid monohydrate (1.14 g) and the mixture heated at reflux for 5 hours. After cooling, 5% w/v sodium bicarbonate solution was added and the mixture extracted with ethyl acetate (3×15 ml). These extracts were washed with 5% v/v sodium bicarbonate solution (2×10 ml), water (2×10 ml) and saturated brine (10 ml), dried (MgSO4) and evaporated. The residue was partially purified by MPLC, eluting with ethyl acetate, to give methyl 4(Z)-6-([2,4,5-cis]-4-o-methylsulphonyloxyphenyl-2[1-(3-pyridyl)-1-methylethyl]-1,3-dioxan-5-yl)hexenoate as an oil (1.03 g). A solution of this oil in THF (6 ml) was treated with 2M sodium hydroxide (10 ml) and heated under reflux with rapid stirring for 6 hours. The mixture was then cooled to ambient temperature and water (10 ml) was added. The mixture obtained was washed with ether (2×20 ml), then acidified to pH 5 with glacial acetic acid and extracted with ether (3×15 ml). These extracts were washed with water (2×10 ml), saturated brine (10 ml), dried (MgSO4) and evaporated. The residue was purified by MPLC, eluting with ethyl acetate/hexane/acetic acid (80:20:1 v/v) to give 4(Z)-6-([2,4,5-cis]-4-o-hydroxyphenyl-2-[1-(3-pyridyl)-1-methylethyl]-1,3-dioxan-5-yl)hexenoic acid (0.5 mole ethyl acetate adduct) as an amorphous solid (789 mg); NMR (CDCl3+D6-DMSO): 1.26 (1.5H, t J=7 Hz), 1.47 (3H, s), 1.49 (3H, s), 1.53 (2H, m), 2.04 (1.5H, s), 2.06 (1H, m), 2.29 (4H, m), 3.86 (1H, dm J=11 Hz), 4.08 (1H, d J=11 Hz), 4.12 (1H, q J=7 Hz), 4.66 (1H, s), 5.10 (1H, m), 5.16 (1H, d J=2 Hz), 5.43 (1H, m), 6.83 (3H, m), 7.11 (1H, m), 7.43 (1H, dd J=7, 5 Hz), 7.90 (1H, dt J=7, 1 Hz), 8.49 (1H, dd J=5, 0.5 Hz), 8.90 (1H, d J=1.5 Hz); m/e 412 (M+H)+; calculated for $C_{24}H_{29}NO_5$, 0.5 $CH_3COOC_2H_5$: C, 68.5; H, 7.3; N, 3.1% found C, 68.1; H, 7.2; N, 2.9%.

The starting aldehyde was obtained as follows:

(1) Solid potassium t-tuboxide (22.4 g) was added under argon to a stirred, ice-cooled, solution of ethyl 3-pyridylacetate (16.5 g) in dry THF (100 ml). The mixture was stirred for 15 minutes and then methyl iodide (12.36 ml) was added dropwise at a rate to maintain the temperature at <20° C. After the addition, the mixture was stirred for 1 hour and then poured into water (200 ml). The mixture was extracted with ether (3×100 ml) and the combined extracts washed with water (2×100 ml), saturated brine (100 ml), dried (MgSO$_4$) and evaporated. The residue was purified by flash chromatography using ether as solvent to give ethyl 2-methyl-2-(3-pyridyl)propionate (A) as a yellow oil (13.56 g); NMR (CDCl$_3$): 1.20 (3H, t J=7 Hz), 1.61 (6H, s), 4.13 (2H, q J=7 Hz), 7.26 (1H, m), 7.67 (1H, dm J=7 Hz), 8.50 (1H, dd J=5, 1 Hz), 8.63 (1H, d J=2 Hz).

(ii) A 1.5M solution of diisobutylaluminium hydride in toluene (21 ml) was added dropwise under argon to a stirred solution of A (1.93 g) in tolune (75 ml) at −70° C. Stirring was continued for 5 minutes after the addition was complete and then a 10% v/v solution of methanol in toluene (15 ml) was added. The mixture obtained was added to water (300 ml), vigorously stirred for 30 minutes and then filtered through kieselguhr. The organic phase was separated and the aqueous phase was saturated with sodium chloride and then extracted with ether (2×100 ml). The combined organic phases were washed with staturated brine (3×100 ml), then dried (MgSO$_4$) and evaporated. Purification of the residue by MPLC, eluting with ethyl acetate, gave 2-methyl-2-(3-pyridyl)propionaldehyde as a clear oil (814 mg); NMR (90 MHz; CDCl$_3$): 1.50 (6H, s), 7.27 (1H, dd J=8, 5 Hz), 7.57 (1H, dt J=8, 2 Hz), 8.52 (2H, m), 9.50 (1H, s).

EXAMPLE 18

Using a similar procedure to that described in Example 17, but starting with 3-(3-pyridyl)-2,2-dimethylpropionaldehyde in place of 2-methyl-2-(3-pyridyl)propionaldehyde, there was obtained, after the final purification by MPLC eluting with 1% v/v acetic acid in ethyl acetate, 4(Z)-6-([2,4,5-cis]-4-o-hydroxyphenyl-2-[2-(3-pyridyl)-1,1-dimethylethyl]-1,3-dioxan-5-yl)hexenoic acid (1 mole acetic acid adduct) as a white foam (56%); NMR (CDCl$_3$): 0.98 (3H, s), 1.01 (3H, s), 1.77 (2H, m), 2.10 (3H, s), 2.38 (4H, m), 2.69 (1H, m), 2.75 (2H, d J=4 Hz), 3.86 (1H, dm J=11 Hz), 4.16 (1H, d J=11 Hz), 4.33 (1H, s), 5.20 (2H, d J=2 Hz), 5.28 (1H, m), 5.47 (1H, m), 6.87 (2H, m), 7.01 (1H, dd J=7, 1.5 Hz), 7.16 (1H, td J=7, 1.5 Hz), 7.27 (1H, dd J=7, 5 Hz), 7.59 (1H, dt J=7, 1 Hz), 8.46 (2H, m); m/e 426 (M+H)$^+$; calculated for C$_{25}$H$_{31}$NO$_5$, CH$_3$COOH: C, 66.8; H, 7.2; N, 2.9%; found C, 67.0; H, 7.4; N, 2.6%.

The starting aldehyde was prepared as follows:

(i) 1.5M Butyllithium in hexane (20 ml) was added dropwise, under argon, to a stirred, cooled (−20° C.) solution of diisopropylamine (4.2 ml) in THF (50 ml). After 10 minutes the mixture was cooled to −70° C. and ethyl isobutyrate (3.99 ml) was added dropwise keeping the temperature <−60° C. Stirring was continued for 20 minutes after completion of the addition then DMPU (15 ml) was added followed by solid 3-chloromethylpyridine hydrochloride (2.0 g). After stirring for 30 minutes at −70° C., the mixture was allowed to warm to 4° C. and was then added to saturated ammonium chloride solution (200 ml). The mixture obtained was extracted with ether (3×100 ml). The combined extracts were washed with brine (50 ml), dried (MgSO$_4$) and evaporated. The residue was purified by flash chromatrography using ether as eluant to give ethyl 3-(3-pyridyl)-2,2-dimethylpropionate (A) as a clear oil (2.12 g); NMR (CDCl$_3$): 1.20 (6H, s), 1.23 (3H, t J=7 Hz), 2.87 (2H, s), 4.12 (2H, q J=7 Hz). 7.20 (1H, J=7, 5 Hz), 7.46 (1H, dt J=7, 1 Hz), 8.40 (1H, d J=1.5 Hz), 8.47 (1H, dd J=5, 1.5 Hz).

(ii) Using an analogous procedure to that in Example 17 (ii), but starting from the above ester A (2.07 g) and using 14 ml of 1.5M diisobutylaluminium hydride, thre was obtained 3-(3-pyridyl)-2,2-dimethylpropionaldehyde (1.04 g); NMR (CDCl$_3$): 1.07 (6H, s), 2.78 (2H, s), 7.18 (1H, dd J=8, 5 Hz), 7.43 (1H, dt J=8, 2 Hz), 8.38 (1H, d J=2 Hz), 8.46 (1H, dd J=5, 1.5 Hz), 9.54 (1H, s).

EXAMPLE 19

Using a similar procedure to that described in Example 17, but starting from methyl 5(Z)-7(4-o-methylsulphonyloxyphenyl-2,2-dimethyl-1,3-dioxan-cis-5-yl)heptanoate, there was thus obtained 5(Z)-7-([2,4,5-cis]-4-o-hydroxyphenyl-2[1-(3-pyridyl)-1-methylethyl]-1,3-dioxan-5-yl)heptenoic acid (47% after recrystallisation from ethyl acetate), m.p. 143°–145° C.; NMR (CDCl$_3$): 1.19 (6H, s), 1.20 (3H, m), 1.52 (3H, m), 1.78 (1H, m), 1.93 (2H, t J=7 Hz), 3.56 (1H, dm J=11 Hz), 3.70 (1H, dd J=11, 1 Hz), 4.39 (1H, s), 4.80 (1H, m), 4.88 (1H, d J=2 Hz), 5.00, (1H, m), 6.52 (2H, m), 6.81 (2H, m), 7.04 (1H, dd, J=7, 5 Hz), 7.60 (1H, dt J=7, 1.5 Hz), 8.17 (1H, dd J=5, 1 Hz), 8.51 (1H, d J=2 Hz); m/e 425 (M+); calculated for C$_{25}$H$_{31}$NO$_5$: C, 70.6; H, 7.3; N, 3.3%; found C, 70.0; H, 7.3; N, 3.2%.

EXAMPLE 20

A solution of methyl 4(Z)-6-([2,4,5-cis]-4-o-methylsulphonyloxyphenyl-2-[3-pyridyloxymethyl]-1,3-dioxan-5-yl)hexenoate (744 mg) in methanol (5 ml) was treated with 2M sodium hydroxide (5 ml) and the mixture vigorously stirred for 2 hours. Water (50 ml) was added and the mixture washed with ether (2×20 ml), then acidified to pH 5 with glacial acetic acid and extracted with ether (3×20 ml). The extracts were washed with water (2×20 ml), saturated brine (20 ml), dried (MgSO$_4$) and evaporated to a small volume from which crystallised 4(Z)6-([2,4,5-cis]-4-o-hydroxyphenyl-2-[3-pyridyloxymethyl]-1,3-dioxan-5-yl)hexenoic acid. Recrystallisation from ethyl acetate gave solid (66 mg) mp 174°–177° C.; NMR (CDCl$_3$+D$_6$-DMSO): 1.56 (1H, m), 1.90 (1H, m), 2.16 (4H, m), 2.42 (1H, m), 3.92 (1H, dm J=11 Hz), 4.03 (1H, dd J=11, 1 Hz), 4.12 (2H, d J=4 Hz), 5.10 (2H, m), 5.22 (1H, d J=2 Hz), 5.30 (1H, m), 6.74 (2H, m), 6.99 (1H, td J=7, 1 Hz), 7.17 (2H, m), 7.23 (1H, dt J=7, 1.5 Hz), 8.12 (1H, dd J=5, 1 Hz), 8.27 (1H, d J=1.5 Hz); m/e 400 (M+H)$^+$; calculated for C$_{22}$H$_{25}$NO$_6$: C, 66.1; H, 6.3; N, 3.5%; found C, 65.7; H, 6.2; N, 3.6%.

The starting ester was prepared as follows:

(i) A solution of 3-hydroxypyridine (4.75 g) in DMPU (10 ml) was added over 30 minutes to a stirred, ice-cooled, suspension of sodium hydride (50% w/w dispersion in mineral oil, 2.4 g) in DMPU (40 ml). The mixture was heated to 50° C. to give a clear solution and then cooled to 4° C. 2-Bromo-1,1-dimethoxyethane (3.53 ml) and potassium iodide (100 mg) were next added and the mixture stirred and heated at 125° C. for 16 hours. The cooled mixture was poured into water (50 ml) and extracted with ether (3×50 ml). The combined extracts were washed with water (2×25 ml), saturated brine (25 ml), dried (MgSO$_4$) and evaporated. Purification by flash chromatography using ether as solvent gave 2-(3-pyridyloxy)-1,1-dimethoxyethane (A) as a yellow oil (1.05 g). NMR (90 MHz; CDCl$_3$): 3.40 (6H, s), 3.97 (2H, d J=5 Hz), 4.65 (1H, t J=5 Hz) 7.14 (2H, m), 8.20 (2H, m).

(ii) A stirred solution of the above acetal A (956 mg) and methyl 4(Z)-6-(4-o-methylsulphonyloxyphenyl-2,2-dimethyl-1,3-dioxan-cis-5-yl)hexenoate (1.435 g) was treated with p-toluenesulphonic acid monohydrate (1.092 g) and the mixture heated at reflux for 3 hours. After cooling, saturated sodium bicarbonate solution (50 ml) was added and the mixture was extracted with ether (3×25 ml). The combined extracts were washed with water (2×25 ml), saturated brine (25 ml), dried (MgSO$_4$) and evaporated. The residue was purified by MPLC, eluting with 75% v/v ethyl acetate in hexane and then by flash chromatography using ether as solvent, to give methyl 4(Z)-6-([2,4,5-cis]-4-o-methylsulphonyloxyphenyl-2-[3-pyridyloxymethyl]-1,3-dioxan-5-yl)hexenoate as a pale yellow oil (775 mg); NMR (CDCl$_3$): 1.58 (1H, m), 1.96 (1H, m), 2.28 (4H, m), 2.50 (1H, m), 3.26 (3H, s), 3.63 (3H, s), 4.01 (1H, dm J=11 Hz), 4.16 (1H, dd J=11, 1 Hz), 4.22 (2H, d J=5 Hz), 5.21 (1H, t H=4 Hz), 5.22 (1H, m), 5.36 (1H, m), 5.37 (1H, d J=2 Hz), 7.28 (5H, m), 7.56 (1H, m), 8.25 (1H, dd J=5, 1 Hz), 8.39 (1H, d J=1.5 Hz); m/e 429 (M+H)$^+$.

EXAMPLE 21

A solution of 1,1-diethoxy-3-(3-pyridyloxy)propane (1.35 g) and 4(Z)-6-(4-o-hydroxyphenyl-2,2-dimethyl-1,3-dioxan-cis-5-yl)hexenoic acid (1.60 g) in acetonitrile (3 ml) was treated with p-toluenesulphonic acid monohydrate (1.33 g) and stirred for 18 hours. 2M Sodium hydroxide (25 ml) was then added and stirring continued for a further 30 minutes. The reaction solution was diluted with water (50 ml), washed with ether (2+50 ml) then acidified to pH 5 with glacial acetic acid and extracted with ether (3+50 ml). The combined extracts were washed with water (2×50 ml), saturated brine (50 ml), dried (MgSO$_4$) and evaporated. Purification of the residue by MPLC, eluting with ethyl acetate/hexane/acetic acid (75:25:1 v/v), gave 4(Z)-6-([2,4,5-cis]-4-o-hydroxyphenyl-2-[2-(3-pyridyloxy)ethyl]-1,3-dioxan-5-yl)hexenoic acid (1 mole acetic acid adduct), as an oil (1.00 g); NMR (CDCl$_3$): 1.68 (H, m), 1.82 (1H, m), 2.10 (3H, s), 2.26 (6H, m), 2.66 (1H, m), 3.92 (1H, dm J=11 Hz), 4.11 (1H, dd J=11, 1 Hz), 4.19 (1H, m), 4.39 (1H, m), 5.03 (1H, t J=4 Hz), 5.21 (1H, m), 5.23 (1H, d J=2 Hz), 5.42 (1H, m), 6.85 (2H, m), 6.97 (1H, dd J=7, 1.5 Hz), 7.16 (1H, td J=7, 1.5 Hz), 7.28 (1H, dd J=8, 5 Hz), 7.42 (1H, dm J=8 Hz), 8.21 (1H, dd J=4, 1 Hz), 8.38 (1H, d J=2 Hz), 8.42 (3H, b); m/e 414 (M+H)$^+$; calculated for C$_{23}$H$_{27}$NO$_6$,CH$_3$COOH: C, 63.4; H, 6.6; N, 2.9%; found: C, 63.1; H, 6.9; N, 2.9%.

The starting acetal was prepared as follows:

3-Hydroxypyridine (2.38 g) was added in protions to a stirred suspension of sodium hydride (1.20 g, 50% w/w dispersion in mineral oil) in DMPU (25 ml). The mixture was heated to 60° C. to give a clear solution and then cooled to ambient temperature. 3-Chloro-1,1-diethoxypropane was then added and stirring continued for 2 days. Water (50 ml) was next added and the resultant mixture extracted with ether (3×25 ml). The combined extracts were washed with water (4×25 ml), saturated brine (25 ml), dried (MgSO$_4$) and evaporated. The residue was purified by flash chromatography in 50% v/v ethyl acetate in hexane to give 3-(3-pyridyloxy)-1,1-diethoxypropane as a clear oil (3.03 g); NMR (CDCl$_3$): 1.21 (6H, t J=7 Hz), 2.11 (2H, q J=6 Hz), 3.62 (4H, m), 4.11 (2H, t J=7 Hz), 4.76 (1H, t J=4 Hz), 7.21 (2H, m), 8.21 (1H, m), 8.32 (1H, t J=1.5 Hz).

EXAMPLE 22

Using a similar procedure to that described in Example 21, but using 1,1-diethoxy-3-[3-(3-pyridyl)propoxy]propane instead of 1,1-diethoxy-3-(3-pyridyloxy)propane and only stirring the reaction mixture for 3 hours, there was obtained after chromatography eluting with 1% v/v acetic acid in ethyl acetate, 4(Z)-6-([2,4,5-cis]-4-o-hydroxyphenyl-2-[2-(3[3-pyridyl]propoxy)ethyl]-1,3-dioxan-5-yl)hexenoic acid (1.5 mole acetic acid adduct) as a pale yellow oil (60%); NMR (CDCl$_3$): 1.66 (1H, m), 1.89 (3H, m), 2.06 (2H, m), 2.10 (4.5H, s), 2.15 (4H, m), 2.72 (3H, m), 3.40 (2H, m), 3.61 (2H, m), 3.88 (1H, bd J=11 Hz), 4.11 (1H, d J=11 Hz), 4.92 (1H, t J=5 Hz), 5.20 (1H, d J=2 Hz), 5.23 (1H, m), 5.45 (1H, m), 6.88 (3H, m), 7.13 (1H, td J=7, 1 Hz), 7.25 (1H, m), 7.59 (1H, m), 7.60 (3.5H, b), 8.45 (2H, m); m/e 456 (M+H)$^+$; calculated for C$_{26}$H$_{33}$NO$_6$,1.5CH$_3$COOH: C, 63.8; H, 7.2; N, 2.6%; found: C, 63.8; H, 7.2; N, 2.4%.

The starting acetal was prepared in a similar manner to that for Example 21, but using 3-(3-pyridyl)propanol instead of 3-hydroxypyridine. There was thus obtained 1,1-diethoxy-3-[3-(3-pyridyl)propoxy]propane as a pale yellow oil (12%); NMR (CDCl$_3$): 1.22 (6H, t J=7 Hz), 1.90 (4H, m), 2.71 (2H, t J=8 Hz), 3.58 (8H, m), 4.66 (1H, t J=4 Hz), 7.21 (1H, dd J=7, 5 Hz), 7.51 (1H, dm J=7 Hz), 8.45 (2H, m).

EXAMPLE 23

Using a similar procedure to that described in Example 17 but starting from 2-methyl-2-(3-pyridyloxy)propionaldehyde there was obtained, after the final purification by MPLC eluting with ethyl acetate/hexane/acetic acid (75:25:1 v/v), 4(Z)-6-([2,4,5-cis]-4-o-hydroxyphenyl-2-[1-(3-pyridyloxy)-1-methylethyl]-1,3-dioxan-5-yl)hexenoic acid as an amorphous solid (30%); NMR (D$_6$-DMSO): 1.34 (6H, s), 1.46 (1H, m), 1.90 (1H, m), 2.15 (4H, m), 2.39 (1H, m), 3.96 (2H, m), 4.81 (1H, s), 5.18 (1H, m), 5.20 (1H, d J=2 Hz), 6.81 (2H, m), 7.19 (5H, m), 7.45 (1H, dm J=7 Hz), 8.27 (2H, m); m/e 427 (M+); calculated for C$_{24}$H$_{29}$NO$_6$: C, 67.4; H, 6.8; N, 3.3%; found: C, 68.0; H, 7.2; N, 2.9%.

The starting aldehyde was prepared as follows:

(i) The procedure of Example 20(i) was repeated using ethyl 2-bromo-2-methylpropionate in place of 2-bromo-1,1-dimethoxyethane but the reaction mixture was stirred for 16 hours at ambient temperature instead of at 125° C. There was thus obtained after flash chromatography eluting with 50% v/v ether in hexane, ethyl 2-methyl-2-(3-pyridyloxy)propionate (A) as an oil (34%,); NMR (CDCl$_3$): 1.27 (3H, t J=7 Hz), 1.61 (6H, s), 4.25 (2H, q J=7 Hz); 7.19 (2H, m), 8.27 (2H, m).

(ii) The procedure of Example 17(ii) was repeated using the above ester A instead of ethyl 2-methyl-2-(3-pyridyl)propionate. There was thus obtained, after MPLC eluting with 50% v/v ethyl acetate in hexane, 2-methyl-2-(3-pyridyloxy)propionaldehyde as a clear oil (56%); NMR (CDCl$_3$): 1.46 (6H, s), 7.20 (2H, m), 8.31 (2H, m), 9.34 (1H, s).

EXAMPLES 24–26

Hydrogenation of a solution of 4(Z)-6-([2,4,5-cis]-4-o-hydroxyphenyl-2-[3-pyridyl]-1,3-dioxan-5-yl)hexenoic acid (621 mg) in ethanol (25 ml) using 10% w/w palladium on carbon (100 mg) for 24 hours at atmospheric pressure, followed by filtration and evaporation of the filtrate gave a yellow oil. Purification by MPLC, eluting with ethyl acetate/hexane/acetic acid (80:20:1 v/v) gave 6-([2,4,5-cis]-4-o-hydroxyphenyl-2-[3-pyridyl]-1,3-dioxan-5-yl)hexanoic acid (1.0 mole acetic acid adduct) (Example 24) as a foam (472 mg); NMR (CDCl$_3$): 1.42 (7H, m), 1.85 (2H, m), 2.11 (3H, s), 2.27 (2H, t J=7 Hz), 4.19 (1H, bd J=11 Hz), 4.34 (1H, bd J=11 Hz), 5.43 (1H, bs), 5.80 (1H, s), 6.87 (2H, m), 7.14 (2H, m), 7.40 (1H, dd J=7, 5 Hz), 7.94 (1H, dt J=7, 1 Hz), 8.04 (2H, b), 8.66 (1H, dd J=4, 1 Hz), 8.80 (1H, d J=2 Hz); m/e 372 (M+H)$^+$; calculated for C$_{21}$H$_{25}$NO$_5$, CH$_3$COOH: C, 65.8; H, 6.7; N, 3.5%; found: C, 65.4; H, 6.9; N, 3.2%.

In a similar manner, but starting from 4(Z)-6-([2,4,5-cis]-4-o-hydroxyphenyl-2-[3-pyridylmethyl]-1,3-dioxan-5-yl)hexenoic acid, there was obtained, after MPLC eluting with ethyl acetate/hexane/acetic acid (90:10:1 v/v), 6-([2,4,5-cis]-4-o-hydroxyphenyl-2-[3-pyridylemthyl]-1,3-dioxan-5-yl)hexanoic acid, (1.0 moles acetic acid adduct) (Example 25) as a white foam (82%); NMR (CDCl$_3$): 1.17 (5H, m), 1.56 (4H, m), 2.10 (3H, s), 2.26 (2H, t J=7 Hz), 3.08 (2H, d J=4 Hz), 3.92 (1H, bd J=11 Hz), 4.15 (1H, d J=11 Hz), 4.96 (1H, t J=5 Hz), 5.14 (1H, d J=2 Hz), 6.88 (3H, m), 7.13 (1H, td J=7, 2 Hz), 7.32 (1H, dd J=7, 5 Hz), 7.70 (1H, dt J=7, 1 Hz), 8.43 (2H, b), 8.51 (1H, dd J=5, 1 Hz), 8.59 (1H, d J=1.5 Hz); m/e 384 (M−H)$^-$; calculated for C$_{22}$H$_{27}$NO$_5$,CH$_3$COOH: C, 64.7; H, 7.0, N, 3.1%; found C, 65.2; H, 7.2; N, 2.9%.

In a similar manner, but starting from 5(Z)-7-([2,4,5-cis]-4-o-hydroxyphenyl-2-[3-pyridylmethyl]-1,3-dioxan-5-yl)heptenoic acid, there was obtained, after flash chromatography using 1% v/v acetic acid in ethyl acetate, 7-([2,4,5-cis]-4-o-hydroxyphenyl-2-2-[3-pyridylmethyl]-1,3-dioxan-5-yl)heptanoic acid (0.5 mole acetic acid adduct) (Example 26) as a white foam (67%); NMR (CDCl$_3$): 1.16 (7H, m), 1.57 (4H, m), 2.10 (1.5H, s), 2.30 (2H, t J=7 Hz), 3.06 (2H, m), 3.92 (1H, bd J=11 Hz), 4.18 (1H, d J=11 Hz), 4.99 (1H, t J=5 Hz), 5.16 (1H, d J=2 Hz), 6.86 (3H, m), 7.13 (1H, td J=7, 1.5 Hz), 7.32 (1H, dd J=7, 5 Hz), 7.68 (1H, dt J=1.5 Hz), 7.83 (2H, b), 8.52 (1H, dd J=5, 1 Hz), 8.67 (1H, d J=1.5 Hz); m/e 400 (M+H)$^+$; calculated for C$_{23}$H$_{29}$NO$_5$,0.5CH$_3$COOH: C, 67.1, H, 7.2, N, 3.3%; found: C, 66.8; H, 7.5; N 3.2%.

EXAMPLE 27

Using a similar procedure to that of Example 3, but starting with 4(Z)-6-([2,4,5-cis]-4-o-methoxyphenyl-2-[2-(3-pyridyl)ethyl]-1,3-dioxan-5-yl)hexenoic acid, there was obtained [after flash chromatography, eluting with 1% v/v acetic acid in ethyl acetate and a further purification by MPLC eluting with dichloromethane/methanol/acetic acid (97:3:1 v/v)] 4(Z)-6-([2,4,5-cis]-4-o-hydroxyphenyl-2-[2-(3-pyridyl)ethyl]-1,3-dioxan-5-yl)hexenoic acid, as a foam (47%); NMR (CDCl$_3$): 1.80 (2H, m), 2.10 (2H, m), 2.37 (4H, m), 2.65 (1H, m), 2.88 (2H, m), 3.90 (2H, bd J=11 Hz), 4.12 (1H, bd J=11 Hz), 4.81 (1, t J=4 Hz), 5.23 (1H, d J=2 Hz), 5.27 (1H, m), 5.47 (1H, m), 6.58 (2H, b), 6.86 (2H, m), 7.00 (1H, dd J=7, 1 Hz), 7.15 (1H, td J=7, 1 Hz), 7.26 (1H, m), 7.61 (1H, bd J=7 Hz), 8.48 (2H, m); m/e 397 (M$^+$); calculated for C$_{23}$H$_{27}$NO$_5$: C, 69.5; H, 6.8; N, 3.5%; found: c, 69.7; H, 7.1; N, 3.0%.

The starting material was obtained as follows:

(i) A stirred solution of oxalyl chloride (1 ml) in dichloromethane (25 ml) under argon was cooled to −60° C. A solution of dimethylsulphoxide (1.7 ml) in dichloromethane (5 ml) was then added dropwise and the temperature maintained at <−50° C. After 2 minutes, a solution of 3-(3-pyridyl)propanol (1.37 g) in dichloromethane (10 ml) was added dropwise during 5 minutes. Stirring was continued for a further 15 minutes and then triethylamine (7.0 ml) was added dropwise. The mixture was allowed to warm to −10° C. and water (50 ml) was then added. The aqueous mixture was extracted with ether (1×100, 2×25 ml) and the combined extracts washed with saturated brine (2×25 ml), then dried (MgSO$_4$) and evaporated. Flash chromatography of the residue, eluting with ethyl acetate, gave 3-(3-pyridyl)propionaldehyde, as a pale yellow oil (630 mg); NMR (90 MHz; CDCl$_3$): 2.85 (4H, m), 7.16 (1H, m), 7.48 (1H, m), 8.40 (2H, m), 9.76 (1H, s).

(ii) A solution of 4(Z)-6-(4-o-methoxyphenyl-2,2-dimethyl-1,3-dioxan-cis-5-yl)hexenoic acid (1.52 g) and 3-(3-pyridyl)propionaldehyde (615 mg) in dichloromethane (10 ml) was treated with p-toluenesulphonic acid monohydrate (952 mg) and the mixture was stirred for 18 hours. 0.1M Sodium hydroxide (25 ml) was added and the mixture was washed with ether (2×10 ml). The aqueous phase was acidified to pH 5 with glacial acetic acid and extracted with ether (3×20 ml). These ether extracts were washed with saturated brine (25 ml), dried (MgSO$_4$) and evaporated to a small volume whereupon 4(Z)-6-([2,4,5-cis]-4-o-methoxyphenyl-2-]2-(3-pyridyl)ethyl]-1,3-dioxan-5-yl)hexenoic acid crystallised as a white solid (987 mg), m.p. 65°–67° C.; NMR (CDCl$_3$): 1.57 (1H, m), 1.84 (1H, m), 2.06 (2H, m), 2.33 (4H, m), 2.52 (1H, m), 2.90 (2H, m), 3.80 (3H, s), 3.90 (1H, dm J=11, 1 Hz), 4.06 (1H, dd J=11, 1 Hz), 4.84 (1H, t J=4 Hz), 5.18 (1H, d J=2 Hz), 5.19 (1H, m), 5.40 (1H, m), 6.84 (1H, bd J=7 Hz), 6.97 (1H, td J=7, 1 Hz), 7.23 (2H, m), 7.32 (1H, dd J=7, 1 Hz), 7.63 (1H, bd J=7 Hz), 8.46 (2H, m); m/e 411 (M$^+$).

EXAMPLE 28

A stirred solution of 4(Z)-6-(4-o-hydroxyphenyl-2,2-dimethyl-1,3-dioxan-cis-5-yl)hexenoic acid (1.51 g) and 3-(4-pyridyl)propionaldehyde (700 mg) in dichloromethane (10 ml) was treated with p-toluenesulphonic acid monohydrate (1.01 g). After 18 hours, the mixture was diluted with ether (40 ml) and extracted with 0.5M sodium hydroxide (1×40 ml, 1×10 ml). The basic solution was acidified to pH 5 with acetic acid and extracted with ethyl acetate (3×50 ml). These extracts were washed with water (2×30 ml), saturated brine (30 ml), dried (MgSO$_4$) and evaporated to give a solid. Recrystallisation from ethanol/hexane (2:3 v/v) gave 4(Z)-6-([2,4,5-cis]-4-o-hydroxyphenyl-2-]2-(4-pyridyl)ethyl]-1,3-dioxan-5-yl)hexenoic acid (1.51 g), m.p. 178°–180° C.; NMR (D$_6$-DMSO): 1.47 (1H, m), 1.91 (3H, m), 2.16 (4H, m), 2.40 (1H, m), 2.80 (2H, m), 3.90 (2H, m), 4.86 (1H, t J=4 Hz), 5.12 (1H, d J=2 Hz), 5.16 (1H, m), 5.34 (1H, m), 6.78 (2H, m), 7.06 (1H, td J=7, 1 Hz), 7.14 (1H, dd J=7, 1 Hz), 7.28 (2H, d J=6 Hz), 8.43 (2H, d J=6 Hz), 9.47 (1H, b); m/e 398 (M+H)$^+$; calculated for C$_{23}$H$_{27}$NO$_5$: C, 69.5; H, 6.8; N, 3.5%; found: C, 69.4; H, 6.9; N, 3.6%.

The starting material was prepared as follows:

(i) 4-Pyridinecarboxaldehyde (4.28 g) was added to a stirred suspension of (carbethoxymethylene)triphenylphosphorane (17.42 g) in toluene (150 ml) at 4° C. Stirring was continued for 5 minutes at 4° C. and then for 1 hour at ambient temperature. The solvent was removed by evaporation and the residue dissolved in ethyl acetate (75 ml). The solution subsequently obtained was cooled in ice-water and the precipitate of triphenylphosphine oxide removed by filtration. The filtrate was extracted with 1M hydrochloric acid (1×50 ml, 1×20 ml). The extracts were neutralised with 2M potassium hydroxide and extracted with ethyl acetate (3×75 ml). These extracts were washed with water (3×50 ml), saturated brine (50 ml), then dried (MgSO$_4$) and evaporated. The solid residue was recrystallised from hexane to give ethyl 3-(4-pyridyl)propenoate (A) (6.37 g), m.p. 64°–66° C. NMR (90 MHz; CDCl$_3$): 1.32 (3H, t J=7 Hz), 4.25 (2H, q J=7 Hz), 6.53 (1H, d J=16 Hz), 7.30 (2H, d J=6 Hz), 7.55 (1H, d J=16 Hz), 8.60 (2H, m). m/e 177 (M+).

(ii) Hydrogenation of a solution of A (5.31 g) in ethanol (75 ml), using 10% w/w palladium on carbon catalyst for 5 hours at atmospheric pressure, followed by filtration and evaporation of the solvent, gave ethyl 3-(4-pyridyl)propionate (B), as a yellow oil (5.28 g); NMR (90 MHz; CDCl$_3$): 1.22 (3H, t J=7 Hz), 2.60 (2H, m), 2.94 (2H, m), 4.10 (2H, q J=7 Hz), 7.08 (2H, d J=6 Hz), 8.45 (2H, d J=6 Hz); m/e 179 (M+).

(iii) A 1.5M solution of diisobutylaluminium hydride in toluene (28 ml) was added dropwise under argon to a stirred solution of B (3.58 g) in toluene (70 ml) at −70° C. Stirring was continued for 30 minutes after the addition was complete and then a 10% v/v solution of methanol in toluene (10 ml) was added. The temperature was allowed to rise to −20° C. Saturated brine (50 ml) was then added and stirring continued for a further 1 hour. The mixture was filtered through kieselguhr. The organic phase was separated and washed with saturated brine (2×25 ml), dried (MgSO$_4$) and evaporated. The residue was purified by flash chromatography, using ethyl acetate as solvent, to give 3-(4-pyridyl)propionaldehyde, as a pale yellow oil 1.88 g); NMR (CDCl$_3$): 2.81 (2H, m), 2.95 (2H, m), 7.13 (2H, dd J=6, 1 Hz), 8.51 (2H, dd J=6, 1 Hz), 9.82 (1H, s); m/e 135 (M+).

EXAMPLE 29

5(Z)-7-([2,4,5-cis]-4-o-methoxyphenyl-2-[2-(4-pyridyl)ethyl]-1,3-dioxan-5-yl)heptenoic acid (1.06 g) was added, under argon, to a stirred solution of lithium diphenylphosphide [prepared from chlorodiphenylphosphine (2.76 g) and lithium metal (350 mg) in dry THF (15 ml)] at 4° C. The mixture was stirred for 5 minutes at 4° C. and then for 3 hours at 50° C. After cooling 10° C., the mixture was then added to ice-water (50 ml). The aqueous mixture was washed with ether (2×30 ml), acidified to pH 5 with glacial acetic acid and extracted with ethyl acetate (3×30 ml). These extracts were washed first with water (2×15 ml), and then with saturated brine (2×15 ml), then dried (MgSO$_4$) and evaporated. The residue was purified by MPLC, eluting with methanol/dichloromethane/acetic acid (5:95:1) to give an oil which crystallised from ehtyl acetate/hexane to give (5(Z)-7-([2,4,5-cis]-4-o-hydroxyphenyl-2-]2-(4-pyridyl)ethyl]-1,3-dioxan-5-yl)-heptenoic acid as a solid (682 mg), m.p. 117°–119° C.; NMR (250 MHz; D$_6$-DMSO): 1.48 (3H, m), 1.91 (5H, m), 2.11 (2H, t J=7 Hz), 2.33 (1H, m), 2.78 (2H, m), 3.90 (2H, m), 4.83 (1H, t J=4 Hz), 5.10 (1H, d J=2 Hz), 5.17 (1H, m), 5.32 (1H, m), 6.79 (2H, m), 7.08 (1H, td J=7, 1 Hz), 7.16 (1H, dd J=7, 1 Hz), 7.28 (2H, d J=4 Hz), 8.46 (2H, b), 9.52 (1H, s); m/e 412 (M+H)+; calculated for C$_{24}$H$_{29}$NO$_5$: C, 70.1; H, 7.1; N, 3.4%; found: C, 69.6; H, 7.1; N, 3.4%.

The starting material was obtained as follows:

A stirred solution of 5(Z)-7-(4-o-methoxyphenyl-2,2-dimethyl-1,3-dioxan-cis-5-yl)heptenoic acid (2.61 g) and 3-(4-pyridyl)propionaldehyde in dichloromethane (15 ml) was treated with p-toluenesulphonic acid monohydrate (1.62 g). After 18 hours, ether (50 ml) was added and the mixture was extracted with 0.5M sodium hydroxide (1×40 ml, 1×10 ml). The basid extracts were acidified to pH 5 with acetic acid and extracted with ethyl acetate (3×75 ml). The extracts were washed with water (2×30 ml), then with saturated brine (30 ml), then dried (MgSO$_4$) and evaporated to give an oil which solidified. Recyrstallisation from ehtyl acetate/hexane gave 5(Z)-7-([2,4,5-cis]-4-o-methoxyphenyl-2-[2-(4-pyridyl)ethyl]-1,3-dioxan-5-yl)heptenoic acid as a solid (2.99 g), m.p. 128°–129° C.; NMR (D$_6$-DMSO): 1.45 (3H, m), 1.82 (3H, m), 2.00 (4H, m), 2.30 (1H, m), 2.78 (2H, m), 3.79 (3H, s), 3.92 (2H, m), 4.84 (1H, t J=4 Hz), 5.13 (1H, d J=2 Hz), 5.22 (2H, m), 6.96 (2H, m), 7.23 (4H, m), 8.46 (2H, b); m/e 426 (M+H)+.

EXAMPLE 30

A stirred solution of 4(Z)-6-(4-o-hydroxyphenyl-2,2-dimethyl-1,3-dioxan-cis-5-yl)hexenoic acid (1.23 g) and 3(3-pyridyl)propenylaldehyde (567 mg) in dichloromethane (10 ml) was treated with p-toluenesulphonic acid monohydrate (811 mg). After 2 hours, 0.5M sodium hydroxide (50 ml) was added and the mixture was washed wtih ether (2×30 ml). The aqueous phase was acidified to pH 5 with acetic acid and extracted with ethyl acetate (3×25 ml). These extracts were washed with water (2×25 ml), then with saturated brine (25 ml), then dried (MgSO$_4$) and evaporated. The residual yellow oil was purified by MPLC [eluting with dichloromethane/methanol/acetic acid (98:2:1 v/v) followed by flash chromatography eluting with ethyl acetate/hexane/acetic acid (50:50:1 v/v)] to give a clear oil, which crystallised on trituration with ether/hexane. Recrystallisation from ethyl acetate/hexane (3:1 v/v) gave 4(Z)-6-([2,4,5-cis]-4-o-hydroxyphenyl-2-[2-(3-pyridyl)ethyl]-1,3-dioxan-5-yl)hexenoic acid as a solid (520 mg), m.p. 142°–143° C.; NMR (250 MHz; CDCl$_3$+D$_6$-DMSO): 1.73 (1H, m), 1.96 (1H, m), 2.30 (4H, m), 2.58 (1H, m), 4.05 (1H, bd J=11 Hz), 4.15 (1H, bd J=11 Hz), 5.21 (1H, m), 5.40 (3H, m), 6.40 (1H, dd J=17, 4 Hz), 6.85 (3H, m), 7.10 (1H, td J=7, 1 Hz), 7.31 (2H, m), 7.81 (1H, m), 8.50 (1H, d J=4 Hz), 8.66 (1H, bs); m/e 396 (M+H)+; calculated for C$_{23}$H$_{25}$NO$_5$: C, 69.9, H, 6.4, N, 3.5%; found: C, 69.7; H, 6.3; N, 3.6%.

The starting aldehyde was prepared as follows:

A stirred mixture of (triphenylphosphoranylidene)acetaldehyde (3.19 g) was 3-pyridinecarboxaldehyde (960 mg) in toluene (50 ml) was heated under argon at reflux for 18 hours and then evaporated. The residue was dissolved in ether (50 ml) and the solution cooled in ice-water. The precipitated triphenylphosphine oxide was removed by filtration and the filtrate evaporated. The residue was dissolved in ethyl acetate (100 ml) and the solution extracted with 1M hydrochloric acid (3×20 ml). The acid extracts were neutralised with 5% v/v sodium bicarbonate solution and then extracted with ether (3×30 ml). The combined extracts were washed with water (2×25 ml), then with saturated brine (25 ml), then dried (MgSO$_4$) and evaporated. The residual oil was purified by flash chromatography, eluting with ethyl acetate, to give 3-(3-pyridyl)propenylaldehyde as a yellow solid (860 mg). [Recrystallisation from ethyl acetate/hexane gave yellow needles of m.p. 65°–68° C.]; NMR (90 MHz;

CDCl$_3$): 6.72 (1H, dd J=16, 7 Hz), 7.33 (1H, dd J=8.5 Hz), 7.46 (1H, d J=16 Hz), 7.85 (1H, dt J=8, 2 Hz), 8.60 (1H, dd J=5, 2 Hz), 8.74 (1H, d J=2 Hz), 9.68 (1H, d J=7 Hz); m/e 134 (M+H)+.

EXAMPLE 31

Using a similar procedure to that of Example 24, but starting from 4(Z)-6-([2,4,5-cis]-4-o-hydroxyphenyl-2-[2-(4-pyridyl)ethyl]-1,3-dioxan-5-yl)hexenoic acid, there was obtained [after MPLC eluting with dichloromethane/methanol/acetic acid (95:5:1 v/v)], 6-([2,4,5-cis]-4-o-hydroxyphenyl-2-[2-(4-pyridyl)ethyl]-1,3-dioxan-5-yl)hexanoic acid (0.5 mole acetic acid adduct) as a white foam (79%); NMR (25 OMHz; D$_6$-DMSO): 0.89 (2H, m), 1.05 (2H, m), 1.28 (3H, m), 1.46 (1H, m), 1.80 (1H, m), 1.90 (1.5H, s), 1.94 (2H, m), 2.08 (2H, t J=7 Hz), 2.76 (2H, m), 3.89 (1H, bd J=11 Hz), 4.01 (1H, d J=11 Hz), 4.81 (1H, t J=5 Hz), 5.05 (1H, d J=2 Hz), 6.77 (2H, m), 7.06 (1H, t J=7, 1 Hz), 7.14 (1H, dd J=7, 1 Hz), 7.28 (2H, d J=6 Hz), 8.43 (2H, d J=6 Hz); m/e 400 (M+H)+; calculated for C$_{23}$H$_{29}$NO$_5$, 0.5 CH$_3$COOH: C, 67.1; H, 7.2; N. 3.3%; found C, 67.0; H, 7.3; N, 3.3%.

EXAMPLE 32

Illustrative pharmaceutical dosage forms inlcude the following table, capsule, injection and aerosol formulations, which may be obtained by conventional procedures well known in the art of pharmacy and are suitable for therapeutic or prophylactic use in humans:

| (a) | Tablet I | mg/tablet |
|---|---|---|
| | Compound X* | 1.0 |
| | Lactose Ph. Eur. | 93.25 |
| | Croscarmellose sodium | 4.0 |
| | Maize starch paste (5% w/v aqueous paste) | 0.75 |
| | Magnesium stearate | 1.0 |

| (b) | Tablet II | mg/tablet |
|---|---|---|
| | Compound X* | 50 |
| | Lactose Ph. Eur | 223.75 |
| | Croscarmellose sodium | 6.0 |
| | Maize starch | 15.0 |
| | Polyvinylpyrrolidone (5% w/v aqueous paste) | 2.25 |
| | Magnesium stearate | 3.0 |

| (c) | Tablet III | mg/tablet |
|---|---|---|
| | Compound X* | 100 |
| | Lactose Ph. Eur. | 182.75 |
| | Croscarmellose sodium | 12.0 |
| | Maize starch paste (5% w/v aqueous paste) | 2.25 |
| | Magnesium stearate | 3.0 |

| (d) | Capsule | mg/capsule |
|---|---|---|
| | Compound X* | 10 mg |
| | Lactose Ph. Eur. | 488.5 |
| | Magnesium stearate | 1.5 |

| (e) | Injection I (50 mg/ml) | |
|---|---|---|
| | Compound X* (free acid form) | 5.0% w/v |
| | 1 M Sodium hydroxide solution | 15.0% v/v |
| | 0.1 M Hydrochloric acid (to adjust pH to 7.6) | |
| | Polyethylene glycol 400 | 4.5% w/v |
| | Water for injection to 100% | |

| (f) | Injection II (10 mg/ml) | |
|---|---|---|
| | Compound X* (free acid form) | 1.0% w/v |
| | Sodium phosphate EP | 3.6% w/v |
| | 0.1 M Sodium hydroxide solution | 15.0% v/v |
| | Water for injection to 100% | |

| (g) | Injection III (1 mg/ml, buffered to pH 6) | |
|---|---|---|
| | Compound X* (free acid form) | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| (h) | Aerosol I | mg/ml |
|---|---|---|
| | Compound X* | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X* | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X* | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

| (k) | Aerosol IV | mg/ml |
|---|---|---|
| | Compound X* | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

Note

§ Compound X is a compound of formula I, or a salt thereof, for example a compound of formula I described in any preceding Examples.

The tablet compositions (a)–(c) may be enteric coated by conventional means, for example to provide a coating of cellulose acetate phthalate. The aerosol compositions (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

Scheme 1
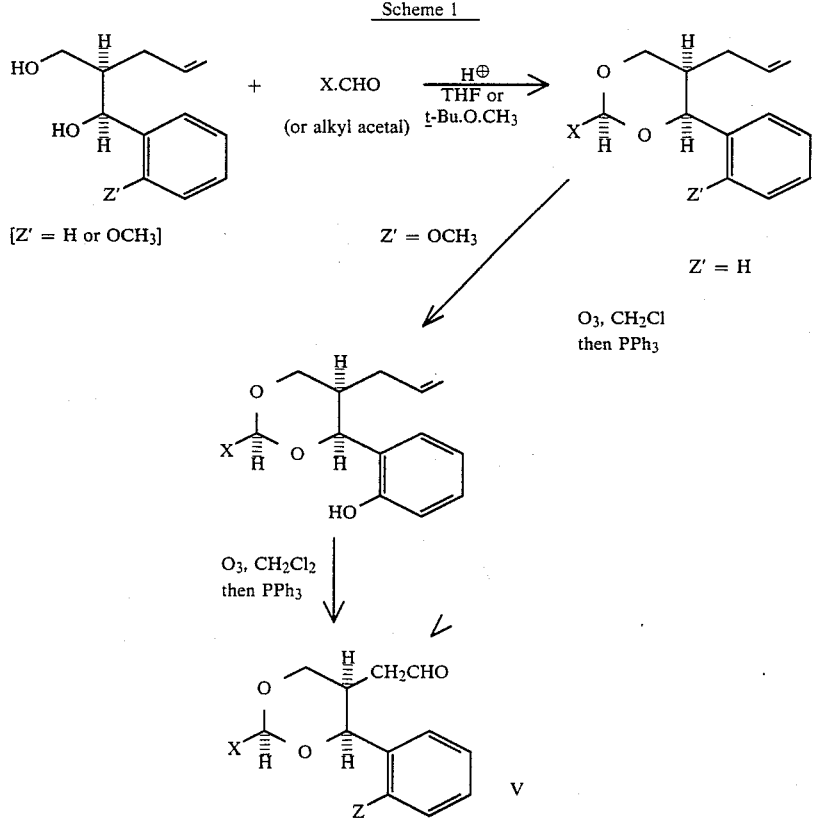
Chemical Formulae of Description
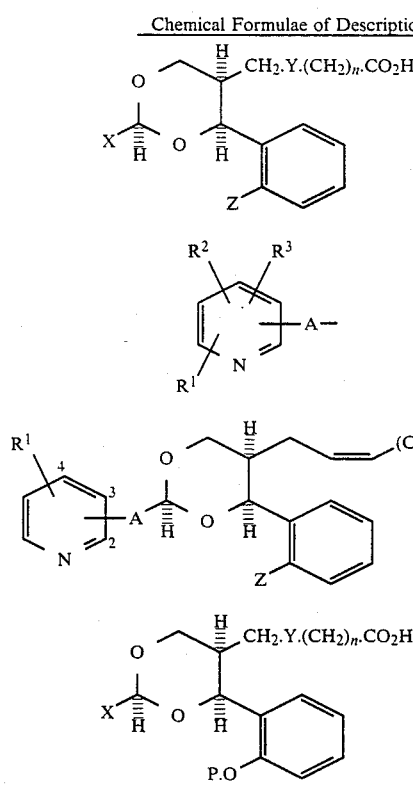
-continued
Chemical Formulae of Description
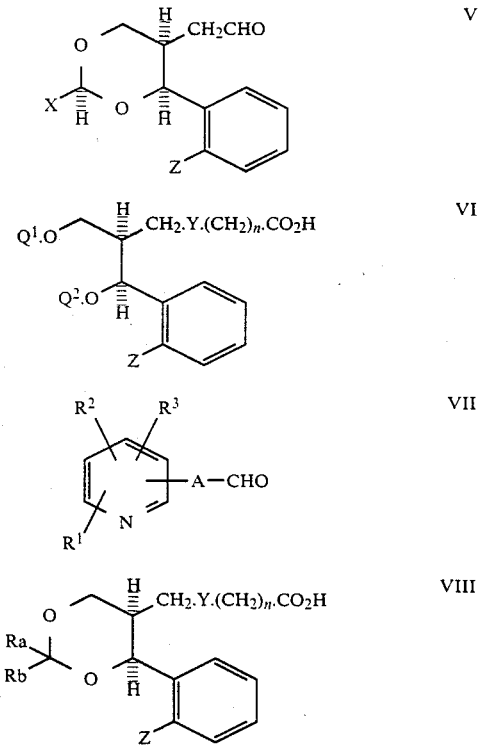
What we claim is:

1. A 1,3-dioxane alkanoic acid derivative of the formula I

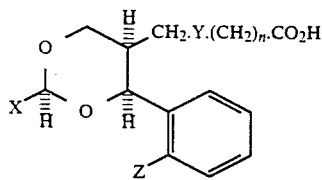

wherein Y is ethylene or vinylene; n is the integer 1, 2, 3 or 4; Z is hydrogen or hydroxy; X is a pyridine containing group of the formula II

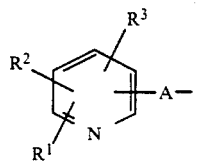

in which A is a linking group selcted from (1-6C)alkylene and (2-6C)alkenylene, either of which may optionally be branched and may optionally contain an oxy link in place of one linking carbon atom, provided that the terminal atom in A attached to the 1,3-dioxane ring is always carbon, or A is a direct link to the 1,3-dioxane ring, and $R^1$, $R^2$ and $R^3$ are independently selected from hydrogen, halogeno, trifluoromethyl, (1-6C)alkoxy and (1-10C)alkyl optionally bearing a carboxy or (1-6C)alkoxy.carbonyl substituent; and wherein the groups at positions 2, 4 and 5 of the 1,3-dioxane ring have cis-relative stereochemistry; or a pharmaceutically acceptable salt thereof.

2. A compound as claimed in claim 1 wherein, in X, A is selected from methylene, ethylene, trimethylene, vinylene, propenylene, isopropylidene, 1,1-dimethylethylene, 2-methyl-1,2-propenylene, methyleneoxymethylene, oxymethylene, oxyethylene, oxyisopropylidene (—O.C(CH$_3$)$_2$—), trimethyleneoxyethylene (—(CH$_2$)$_3$.O.(CH$_2$)$_2$—) and a grouop of the formula —CH$_2$.O.CH$_2$.C(CH$_3$)$_2$— or —O.CH$_2$.C(CH$_3$)$_2$—; and $R^1$, $R^2$ and $R^3$ are independently selected from hydrogen, trifluoromethyl, fluoro, chloro, bromo, methoxy, ethoxy, propoxy, butoxy, methyl, ethyl, propyl, isopropyl, butyl, pentyl, hexyl, heptyl, octyl, nonyl and decyl, any of the latter six groups optionally bearing a carboxy, methoxycarbonyl or ethoxycarbonyl substituent.

3. A compound as claimed in claim 1 wherein, in X, A is a direct bond, methylene, isopropylidene, ethylene, 1,1-dimethylethylene oxymethylene, oxyethylene or oxyisopropylidene.

4. A compound of the formula

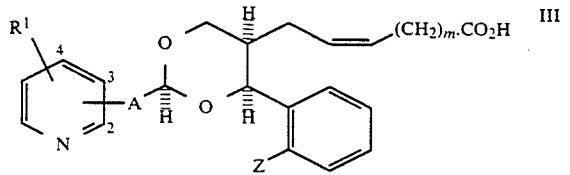

wherein A, Z and $R^1$ have any of the meanings defined in claim 1, m is the integer 2 or 3, and the groups at positions 2, 4 and 5 of the 1,3-dioxane ring have cis-relative stereochemistry, or a pharmaceutically acceptable salt thereof.

5. A compound as claimed in claim 4 wherein Z is hydroxy and the linking group A is selected from a direct bond, methylene, ethylene, isopropylidene, 1,1-dimethylethylene and oxyisopropylidene, and is attached to the 3 or 4 position of the pyridine moiety.

6. A compound as claimed in claim 4 wherein Z is hydroxy, the linking group A is ethylene or vinylene and is attached to the 3 or 4 position of the pyridine moiety.

7. A compound as claimed in claim 4 wherein Z is hydroxy, the linking group A is selected from a direct bond, methylene, isopropylidene, 1,1-dimethylethylene and oxyisopropylidene and is attached to the 2 position of the pyridine moiety, and m is the integer 2.

8. A compound as claimed in claim 5 wherein the linking group A has a disubstituted methylene adjacent to the dioxane ring and $R^1$, $R^2$ and $R^3$ are hydrogen.

9. A compound as claimed in claim 7 wherein the linking group A has a disubstituted methylene adjacent to the dioxane ring and $R^1$, $R^2$ and $R^3$ are hydrogen.

10. A compound as claimed in claim 1 wherein Z is hydrogen, n is the integer 2 or 3 and, in X, the linking group A is attached to the 3 or 4 position of the pyridine moiety.

11. A compound as claimed in claim 10 wherein a is a direct bond or methylene.

12. A compound selected from the group consisting of:
  4(Z)-6-([2,4,5-cis]-4-o-hydroxyphenyl-2-[3-pyridyl]-1,3-dioxan-5-yl)hexenoic acid;
  5(Z)-7-([2,4,5-cis]-4-o-hydroxyphenyl-2-[3-pyridylmethyl]-1,3-dioxan-5-yl)heptenoic acid;
  4(Z)-6-([2,4,5-cis]-4-o-hydroxyphenyl-2-[3-pyridylmethyl]-1,3-dioxan-5-yl)hexenoic acid;
  4(Z)-6-([2,4,5-cis]-4-o-hydroxyphenyl-2-[1-(3-pyridyl)-1-methylethyl]-1,3-dioxan-5-yl)hexenoic acid;
  4(Z)-6-([2,4,5-cis]-4-o-hydroxyphenyl-2-[2-(3-pyridyl)-1,1-dimethylethyl]-1,3-dioxan-5-yl)hexenoic acid;
  5(Z)-7-([2,4,5-cis]-4o-hydroxyphenyl-2-[1-(3-pyridyl)-1-methylethyl]-1,3-dioxan-5-yl)heptenoic acid;
  4(Z)-6-([2,4,5-cis]-4o-hydroxyphenyl-2-[1-(3-pyridyloxy)-1-methylethyl]-1,3-dioxan-5-yl)hexenoic acid;
  4(Z)-6-([2,4,5-cis]-4-o-hydroxyphenyl-2-[2-pyridyl]-1,3-dioxan-5-yl)hexenoic acid;
  4(Z)-6-([2,4,5-cis]-4-o-hydroxyphenyl-2-[2-pyridylmethyl]-1,3-dioxan-5-yl)hexenoic acid;
  6(Z)-8-([2,4,5-cis]-4-o-hydroxyphenyl-2-[4-pyridyl]-1,3-dioxan-5-yl)octenoic acid;
  5(Z)-7-([2,4,5-cis]-4-phenyl-2-[3-pyridylmethyl]-1,3-dioxan-5-yl)heptenoic acid; or a pharmaceutically acceptable salt thereof.

13. A salt as claimed in claim 1 selected from alkali metal and alkaline earth metal salts, ammonium and aluminium salts, salts with organic amines and quaternary bases forming physiologically acceptablt cations, and also salts with acids affording physiologically acceptable anions.

14. A method of producing a beneficial effect on the thromboxane A$_2$ system by antagonishing one or more of the actions of thromboxane A$_2$ and/or inhibiting its synthesis in a warm-blooded animal which requires such treatment said method comprising administering to said animal an effective amount of a compound of the formula I or III, or a pharmaceutically acceptable salt thereof, as claimed in claim 1.

15. A pharmaceutical composition for producing a beneficial effect on the thromboxane $A_2$ system by antagonizing one or more of the actions of thromboxane $A_2$ and/or inhibiting its synthesis which comprises an amount of a compound of the formula I or III, or a pharmaceutically acceptable salt thereof, as claimed in claim 1 or 4, sufficient to exert said effect together with a pharmaceutically acceptable diluent or carrier.

* * * * *